United States Patent
White et al.

(10) Patent No.: US 11,786,308 B2
(45) Date of Patent: Oct. 17, 2023

(54) ORTHOPAEDIC IMPLANT PLACEMENT SYSTEM AND METHOD

(71) Applicant: DePuy Synthes Products, Inc., Raynham, MA (US)

(72) Inventors: Stephen E. White, Fort Wayne, IN (US); William J. Maloney, Palo Alto, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 451 days.

(21) Appl. No.: 16/863,142

(22) Filed: Apr. 30, 2020

(65) Prior Publication Data
US 2020/0345421 A1 Nov. 5, 2020

Related U.S. Application Data

(60) Provisional application No. 62/842,201, filed on May 2, 2019.

(51) Int. Cl.
*A61B 34/10* (2016.01)
*A61F 2/38* (2006.01)
*A61B 34/20* (2016.01)

(52) U.S. Cl.
CPC .............. *A61B 34/10* (2016.02); *A61B 34/20* (2016.02); *A61F 2/38* (2013.01); *A61B 2034/102* (2016.02); *A61B 2034/105* (2016.02); *A61B 2034/2055* (2016.02)

(58) Field of Classification Search
CPC ... A61B 34/10; A61B 34/20; A61B 2034/102; A61B 2034/105; A61B 2034/2055; A61F 2/3868; A61F 2002/3895
See application file for complete search history.

(56) References Cited

U.S. PATENT DOCUMENTS

| | | | |
|---|---|---|---|
| 3,748,662 A | 7/1973 | Helfet | |
| 5,219,362 A | 6/1993 | Tuke et al. | |
| 5,370,701 A | 12/1994 | Finn | |

(Continued)

FOREIGN PATENT DOCUMENTS

| | | | |
|---|---|---|---|
| EP | 1604623 B1 | 6/2008 | |
| EP | 2572677 B1 | 7/2015 | |

(Continued)

OTHER PUBLICATIONS

PCT International Search Report for International Application No. PCT/IB20/54105, dated Aug. 31, 2020; 3 pages.

(Continued)

*Primary Examiner* — Anu Ramana
(74) *Attorney, Agent, or Firm* — Barnes & Thornburg LLP

(57) ABSTRACT

A surgical planning computing system and related surgical method include identifying an anatomical landmark of a patient's bony anatomy in a three-dimensional anatomical image and determining positioning criteria for an orthopedic prosthesis to be implanted into the patient's bony anatomy. The positioning criteria may define an alignment between the anatomical landmark and a feature of the orthopaedic prosthesis. A three-dimensional model of the orthopaedic prosthesis is positioned in the three-dimensional model based on the positioning criteria to provide a surgical plan for the implantation of the orthopaedic prosthesis.

20 Claims, 18 Drawing Sheets

(56) References Cited

U.S. PATENT DOCUMENTS

| | | | |
|---|---|---|---|
| 5,682,886 A * | 11/1997 | Delp | A61B 90/36 600/407 |
| 5,871,018 A * | 2/1999 | Delp | A61B 17/154 128/898 |
| 5,964,808 A | 10/1999 | Blaha et al. | |
| 6,013,103 A | 1/2000 | Kaufman et al. | |
| 7,261,740 B2 | 8/2007 | Tuttle et al. | |
| 8,187,335 B2 | 5/2012 | Wyss et al. | |
| 3,192,498 A1 | 6/2012 | Wagner et al. | |
| 8,236,061 B2 | 8/2012 | Heldreth et al. | |
| 8,328,873 B2 | 12/2012 | Metzger et al. | |
| 8,480,752 B2 | 7/2013 | Dun | |
| 8,480,762 B2 | 7/2013 | Yoshimitsu | |
| 8,628,579 B2 | 1/2014 | Ries et al. | |
| 8,784,496 B2 | 7/2014 | Wagner et al. | |
| 8,795,380 B2 | 8/2014 | Heldreth et al. | |
| 8,828,086 B2 | 9/2014 | Williams et al. | |
| 8,834,575 B2 | 9/2014 | Wyss et al. | |
| 8,915,965 B2 | 12/2014 | Komistek | |
| 9,101,393 B2 * | 8/2015 | Jordan | A61B 17/56 |
| 9,101,394 B2 * | 8/2015 | Arata | G16Z 99/00 |
| 9,168,145 B2 | 10/2015 | Wyss et al. | |
| 9,216,088 B2 | 12/2015 | Wasielewski | |
| 9,220,601 B2 | 12/2015 | Williams et al. | |
| 9,299,138 B2 * | 3/2016 | Zellner | G16H 30/20 |
| 9,320,616 B2 | 4/2016 | Samuelson et al. | |
| 9,320,624 B2 | 4/2016 | Shin | |
| 9,326,864 B2 | 5/2016 | Wyss et al. | |
| 9,402,726 B2 * | 8/2016 | Linderman | A61B 17/155 |
| 9,452,053 B2 | 9/2016 | Wagner et al. | |
| 9,539,099 B2 | 1/2017 | Heldreth et al. | |
| 9,603,711 B2 * | 3/2017 | Bojarski | A61B 17/155 |
| 9,668,870 B2 | 6/2017 | Wasielewski | |
| 9,788,954 B2 | 10/2017 | Parisi et al. | |
| 9,820,821 B2 * | 11/2017 | Aram | A61B 34/10 |
| 9,861,446 B2 * | 1/2018 | Lang | A61B 17/1778 |
| 9,931,216 B2 | 4/2018 | Williams et al. | |
| 9,937,049 B2 | 4/2018 | Wyss et al. | |
| 9,962,264 B2 | 5/2018 | Komistek | |
| 10,080,663 B2 | 9/2018 | Wasielewski | |
| 10,159,530 B2 * | 12/2018 | Lang | A61B 17/1778 |
| 10,179,051 B2 | 1/2019 | Heldreth et al. | |
| 10,179,052 B2 | 1/2019 | Clary et al. | |
| 10,201,429 B2 | 2/2019 | Enomoto et al. | |
| 10,265,180 B2 | 4/2019 | Wyss et al. | |
| 10,278,827 B2 | 5/2019 | Drury et al. | |
| 10,478,307 B2 | 11/2019 | Wasielewski et al. | |
| 10,543,098 B2 | 1/2020 | Williams et al. | |
| 10,729,551 B2 | 8/2020 | Heldreth et al. | |
| 10,849,760 B2 | 12/2020 | Wyss et al. | |
| 11,229,485 B2 * | 1/2022 | Otto | A61B 5/1075 |
| 11,324,598 B2 * | 5/2022 | Dai | A61F 2/3094 |
| 11,337,823 B2 | 5/2022 | Williams et al. | |
| 11,364,081 B2 * | 6/2022 | Dees, Jr. | A61B 17/155 |
| 11,369,478 B2 | 6/2022 | Wyss et al. | |
| 2003/0009228 A1 | 1/2003 | Figueroa et al. | |
| 2005/0107886 A1 | 5/2005 | Crabtree et al. | |
| 2005/0278035 A1 * | 12/2005 | Wyss | A61F 2/3886 623/20.29 |
| 2008/0262812 A1 * | 10/2008 | Arata | A61B 90/36 703/11 |
| 2008/0269596 A1 * | 10/2008 | Revie | A61B 90/39 705/28 |
| 2009/0088860 A1 | 4/2009 | Romeis et al. | |
| 2009/0204221 A1 | 8/2009 | Walker | |
| 2010/0036499 A1 | 2/2010 | Pinskerova | |
| 2010/0286788 A1 | 11/2010 | Komistek | |
| 2012/0265496 A1 * | 10/2012 | Mahfouz | A61B 17/14 606/89 |
| 2012/0310362 A1 | 12/2012 | Li et al. | |
| 2013/0006373 A1 | 1/2013 | Wyss et al. | |
| 2013/0197653 A1 | 8/2013 | Hawkins et al. | |
| 2013/0197654 A1 | 8/2013 | Samuelson et al. | |
| 2014/0039635 A1 | 2/2014 | Bartels et al. | |
| 2014/0081412 A1 | 3/2014 | Metzger | |
| 2014/0330388 A1 | 11/2014 | Mizuguchi et al. | |
| 2015/0088264 A1 | 3/2015 | Li et al. | |
| 2015/0190235 A1 | 7/2015 | Mcminn | |
| 2016/0030184 A1 | 2/2016 | Whiteside | |
| 2016/0317312 A1 | 11/2016 | Bojarski et al. | |
| 2017/0079801 A1 * | 3/2017 | Drury | A61F 2/389 |
| 2017/0128219 A1 | 5/2017 | Metzger et al. | |
| 2017/0189191 A1 | 7/2017 | Heldreth et al. | |
| 2017/0189195 A1 | 7/2017 | Blaha | |
| 2017/0266013 A1 | 9/2017 | Enomoto et al. | |
| 2017/0340389 A1 * | 11/2017 | Otto | A61B 5/1077 |
| 2019/0209331 A1 | 7/2019 | Varadarajan et al. | |
| 2019/0209333 A1 | 7/2019 | Drury et al. | |
| 2019/0240032 A1 | 8/2019 | Wasielewski et al. | |
| 2020/0069432 A1 | 3/2020 | Mcminn | |
| 2020/0085583 A1 | 3/2020 | Hodge | |
| 2020/0100902 A1 | 4/2020 | Wasielewski et al. | |
| 2020/0214843 A1 * | 7/2020 | Radermacher | G05B 19/4099 |
| 2022/0079678 A1 * | 3/2022 | McKinnon | G06N 20/10 |

FOREIGN PATENT DOCUMENTS

| | | | |
|---|---|---|---|
| WO | WO-9723172 A2 * | 7/1997 | ........... A61B 17/154 |
| WO | WO-2010151564 A1 * | 12/2010 | ........... A61B 17/155 |
| WO | WO-2011075697 A2 * | 6/2011 | ............... A61F 2/30 |
| WO | 2014143538 A1 | 9/2014 | |
| WO | 2017160889 A1 | 9/2017 | |
| WO | 2017204832 A1 | 11/2017 | |
| WO | WO-2017204832 A1 * | 11/2017 | ......... A61B 17/3209 |

OTHER PUBLICATIONS

International SR and Written Opinion for International App. No. PCT/US2020/022123, Completed May 8, 2020, 13 Pages.

International SR and Written Opinon for International App. No. PCT/US2020/022119, Completed May 27, 2020, 11 Pages.

PCT International SR for International App. No. PCT/IB20/54110, Aug. 12, 2020, 3 Pages.

Advance, Medial-Pivot and Stemmed Medial-Pivot Knee Systems, Wright Medical Technology, Inc., 2010, 12 pages.

Persona, The Personalized Knee, Surgical Technique, Zimmer Biomet, 2018, 76 pages.

Persona, The Personalized Knee, Medial Congruent Bearing Design Rationale, Zimmer Biomet, 2017, 20 pages.

eMP, Evolution, Medial-Pivot Knee System, The ACL-PCL Substituting Knee, Key Aspects, MicroPort Orthopaedics, 2015, 6 pages.

Evolution, Medial-Pivot Knee System, Surgical Technique, Distal Cut First, MicroPort Orthopaedics, 2014, 52 pages.

PCT Search Report & Written Opinion prepared for PCT/EP2021/069244, dated Nov. 1, 2022, 24 pages.

Smith & Nephew, Journey II TKA Total Knee System—Combined Technique for Journey II BCS and Journey II CR, 68 pages.

* cited by examiner

ORTHOPAEDIC IMPLANT PLACEMENT SYSTEM AND METHOD

CROSS-REFERENCE TO RELATED APPLICATIONS

The present patent application claims priority to and the benefit of U.S. Provisional Patent Application Ser. No. 62/842,201 entitled "ORTHOPAEDIC IMPLANT PLACEMENT SYSTEM AND METHOD," which was filed on May 2, 2019 and which is expressly incorporated by reference in its entirety into this application.

TECHNICAL FIELD

The present invention relates to orthopaedic surgical procedures and, more particularly, to the placement of orthopaedic prostheses during performance of an orthopaedic surgical procedure.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial insert in cases wherein it is desirable to limit the movement of the knee prosthesis, such as when significant soft tissue damage or loss is present. Alternatively, the knee prosthesis may include a "mobile" tibial insert in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue may cause unwanted or undesirable motion of the orthopaedic knee prosthesis. For example, the orthopaedic knee prosthesis may exhibit an amount of unnatural (paradoxical) anterior translation as the femoral component is moved through the range of flexion.

To ensure the functionality of an orthopaedic knee prosthesis, proper positioning of the orthopaedic knee prosthesis onto the patient's bony anatomy must be achieved. However, because each patent's boney anatomy is different, each corresponding orthopaedic surgical procedure is different. As such, orthopaedic surgeons may rely on pre-operative surgical planning to facilitate the proper positioning of orthopaedic knee prosthesis. Typical pre-operative surgical plans may include, for example, a step-by-step plan for the orthopaedic surgical procedure, which may include the resectioning of the patient's bone, the implantation and alignment of the orthopaedic knee prosthesis, and so forth. Typical pre-operative surgical planning may be a manual process or may be supported by computer-aided planning.

SUMMARY

According to an aspect of the present disclosure, a surgical planning computing system for generating a surgical plan for an orthopaedic surgical procedure is disclosed. The surgical planning computing system may include one or more processors and memory. The memory may have stored therein a plurality of instructions that, in response to execution, cause the computing system to identify an anatomical landmark of a patient's bony anatomy in a three-dimensional anatomical image of the patient's bony anatomy and determine positioning criteria for an orthopaedic prosthesis that is to be used in the orthopaedic surgical procedure. The positioning criteria may identify an alignment between the anatomical landmark and a feature of the orthopaedic prosthesis. The plurality of instructions, in response to execution, may further cause the computing system to position a three-dimensional model of the orthopaedic prosthesis in the three-dimensional anatomical image based on the positioning criteria to generate an updated three-dimensional anatomical image that includes the three-dimensional model of the orthopaedic prosthesis and display the updated three-dimensional anatomical image.

In some embodiments, the patient's bony anatomy may include a femur and the orthopaedic prosthesis may include a femoral component. In such embodiments, to position the three-dimensional model of the orthopaedic prosthesis may include to position a three-dimensional model of the femoral component in the three-dimensional anatomical image such that an articular surface of a condyle of the femoral component that is defined by a constant radius of curvature is aligned with a posterior articular surface of a condyle of the patient's femur included in the three-dimensional anatomical image. Alternatively, in such embodiments, to position the three-dimensional model of the orthopaedic prosthesis may include to position a three-dimensional model of the femoral component in the three-dimensional anatomical image such that an articular surface of a condyle of the femoral component that is defined by a constant radius of curvature is aligned with an anterior articular surface of a condyle of the patient's femur included in the three-dimensional anatomical image.

Additionally, in embodiments in which patient's bony anatomy includes a femur and the orthopaedic prosthesis is embodied as a femoral component, to position the three-dimensional model of the orthopaedic prosthesis may include to position a three-dimensional model of the femoral component in the three-dimensional anatomical image such that an articular surface of a patellofemoral surface of the femoral component is aligned with a patellofemoral surface of the patient's femur included in the three-dimensional anatomical image. Alternatively, in such embodiments, to position the three-dimensional model of the orthopaedic prosthesis may include to position a three-dimensional model of the femoral component in the three-dimensional anatomical image such that a center of a constant radius of curvature that defines an articular surface of a condyle of the femoral component is offset from an anatomical center of the medial epicondyle of the patient's femur included in the three-dimensional anatomical image by a reference amount. Alternatively still, in such embodiments, to position the three-dimensional model of the orthopaedic prosthesis may include to position a three-dimensional model of the femoral component in the three-dimensional anatomical image such that a center of a constant radius of curvature that defines an articular surface of a condyle of the femoral component is offset from an anatomical center of the lateral epicondyle of the patient's femur included in the three-dimensional anatomical image by a reference amount.

In some embodiments, the patient's bony anatomy may include a tibia and the orthopaedic prosthesis may include a tibial component. In such embodiments, to position the three-dimensional model of the orthopaedic prosthesis may include to position a three-dimensional model of the tibial component in the three-dimensional anatomical image such that a dwell point of an articular surface of the tibial component is aligned with a dwell point of a tibial plateau of the patient's tibia included in the three-dimensional anatomical image.

Additionally, in some embodiments, the positioning criteria may identify a feature of the orthopaedic prosthesis that is to be aligned with the anatomical landmark in the three-dimensional anatomical image. Additionally or alternatively, the positioning criteria may identify an amount of an offset between a dwell point of an articular surface of the orthopaedic prosthesis and a dwell point of a bone of the patient's bony anatomy. Further, in some embodiments, the plurality of instructions, in response to execution, may further cause the computing system to generate positioning data that defines orthopaedic coordinates at which the feature of the orthopaedic prosthesis should be located on a bone of the patient's anatomy.

According to another aspect, a method for performing an orthopaedic surgery on a patient is disclosed. The method may include obtaining a three-dimensional anatomical image of a bone of the patient in which an orthopaedic prosthesis is to be implanted during the orthopaedic surgery and operating a surgical planning computing system to (i) identify an anatomical landmark of the bone of the patient in the three-dimensional anatomical image, (ii) select positioning criteria for the orthopaedic prosthesis, wherein the positioning criteria identifies an alignment between the anatomical landmark of the bone of the patient and a feature of the orthopaedic prosthesis, and (iii) position a three-dimensional model of the orthopaedic prosthesis in the three-dimensional anatomical image based on the positioning criteria to generate an updated three-dimensional anatomical image that includes the three-dimensional model of the orthopaedic prosthesis. The method may also include performing the orthopaedic surgery to implant the orthopaedic prosthesis into the patient's bone using the updated three-dimensional anatomical image as a surgical plan for the orthopaedic surgery.

In some embodiments, the patient's bony anatomy may include a femur and the orthopaedic prosthesis may include a femoral component. In such embodiments, to position the three-dimensional model of the orthopaedic prosthesis may include to position a three-dimensional model of the femoral component in the three-dimensional anatomical image such that an articular surface of a condyle of the femoral component that is defined by a constant radius of curvature is aligned with a posterior articular surface of a condyle of the patient's femur included in the three-dimensional anatomical image. Alternatively, in such embodiments, to position the three-dimensional model of the orthopaedic prosthesis may include to position a three-dimensional model of the femoral component in the three-dimensional anatomical image such that an articular surface of a condyle of the femoral component that is defined by a constant radius of curvature is aligned with an anterior articular surface of a condyle of the patient's femur included in the three-dimensional anatomical image.

Additionally, in embodiments in which patient's bony anatomy includes a femur and the orthopaedic prosthesis is embodied as a femoral component, to position the three-dimensional model of the orthopaedic prosthesis may include to position a three-dimensional model of the femoral component in the three-dimensional anatomical image such that an articular surface of a patellofemoral surface of the femoral component is aligned with a patellofemoral surface of the patient's femur included in the three-dimensional anatomical image. Alternatively, in such embodiments, to position the three-dimensional model of the orthopaedic prosthesis may include to position a three-dimensional model of the femoral component in the three-dimensional anatomical image such that a center of a constant radius of curvature that defines an articular surface of a condyle of the femoral component is offset from an anatomical center of the medial epicondyle of the patient's femur included in the three-dimensional anatomical image by a reference amount. Alternatively still, in such embodiments, to position the three-dimensional model of the orthopaedic prosthesis may include to position a three-dimensional model of the femoral component in the three-dimensional anatomical image such that a center of a constant radius of curvature that defines an articular surface of a condyle of the femoral component is offset from an anatomical center of the lateral epicondyle of the patient's femur included in the three-dimensional anatomical image by a reference amount.

In some embodiments, the patient's bony anatomy may include a tibia and the orthopaedic prosthesis may include a tibial component. In such embodiments, to position the three-dimensional model of the orthopaedic prosthesis may include to position a three-dimensional model of the tibial component in the three-dimensional anatomical image such that a dwell point of an articular surface of the tibial component is aligned with a dwell point of a tibial plateau of the patient's tibia included in the three-dimensional anatomical image.

Additionally, in some embodiments, the positioning criteria may identify a feature of the orthopaedic prosthesis that is to be aligned with the anatomical landmark in the three-dimensional anatomical image. Additionally or alternatively, the positioning criteria may identify an amount of an offset between a dwell point of an articular surface of the orthopaedic prosthesis and a dwell point of a bone of the patient's bony anatomy. Further, in some embodiments, the plurality of instructions, in response to execution, may further cause the computing system to generate positioning data that defines orthopaedic coordinates at which the feature of the orthopaedic prosthesis should be located on a bone of the patient's anatomy.

According to a further aspect of the disclosure, one or more non-transitory, machine-readable storage media comprising a plurality of instructions stored thereon is disclosed. The plurality of instructions, in response to execution by a computing system, cause the computing system to identify an anatomical landmark of a patient's bony anatomy in a three-dimensional anatomical image of the patient's bony anatomy and determine positioning criteria for an orthopaedic prosthesis that is to be used in an orthopaedic surgical procedure. The positioning criteria may identify an alignment between the anatomical landmark and a feature of the orthopaedic prosthesis. The plurality of instructions, in response to execution, further cause the computing system to position a three-dimensional model of the orthopaedic prosthesis in the three-dimensional anatomical image based on the positioning criteria to generate an updated three-dimensional anatomical image that includes the three-dimensional model of the orthopaedic prosthesis and display the updated three-dimensional anatomical image.

In some embodiments, the patient's bony anatomy may include a femur and the orthopaedic prosthesis may include a femoral component. In such embodiments, to position the three-dimensional model of the orthopaedic prosthesis may include to position a three-dimensional model of the femoral component in the three-dimensional anatomical image such that an articular surface of a condyle of the femoral component that is defined by a constant radius of curvature is aligned with an articular surface of a condyle of the patient's femur included in the three-dimensional anatomical image. Alternatively, in such embodiments, to position the three-dimensional model of the orthopaedic prosthesis comprises to position a three-dimensional model of the femoral component in the three-dimensional anatomical image such that a center of a constant radius of curvature that defines an articular surface of a condyle of the femoral component is offset from an anatomical center of the medial or lateral epicondyle of the patient's femur included in the three-dimensional anatomical image by a reference amount.

Additionally, in some embodiments, the patient's bony anatomy may include a tibia and the orthopaedic prosthesis may include a tibial component. In such embodiments, to position the three-dimensional model of the orthopaedic prosthesis may include to position a three-dimensional model of the tibial component in the three-dimensional anatomical image such that a dwell point of an articular surface of the tibial component is aligned with a dwell point of a tibial plateau of the patient's tibia included in the three-dimensional anatomical image.

According to yet a further aspect of the disclosure, a surgical planning computing system for generating a surgical plan for an orthopaedic surgical procedure includes one or more processors and a memory having stored therein a plurality of instructions. In response to execution, the plurality of instructions cause the surgical planning computing system to identify a dwell point of a medial tibial plateau of a patient's tibia captured in a three-dimensional anatomical image of the patient's bony anatomy and identify a center of rotation of a medial condyle of a patient's femur a captured in the three-dimensional anatomical image.

Additionally, the plurality of instructions, when executed, cause the surgical planning computing system to determine positioning criteria for a medial pivoting orthopaedic prosthesis that is to be used in the orthopaedic surgical procedure. The medial pivoting orthopaedic prosthesis includes a tibial insert and a femoral component. The positioning criteria identifies (i) an alignment between the dwell point of the medial articular surface of the tibial insert and the dwell point of the medial tibial plateau of the patient's tibia and (ii) an alignment of a feature of a medial condyle of the femoral component based on the center of rotation of the medial condyle of the patient's femur.

The plurality of instructions, when executed, may also cause the surgical planning computing system to position a three-dimensional model of the tibial insert and of the femoral component in the three-dimensional anatomical image based on the positioning criteria to generate an updated three-dimensional anatomical image that includes the three-dimensional model of the orthopaedic prosthesis. Additionally, the plurality of instructions, when executed, may cause the surgical planning computing system to display the updated three-dimensional anatomical image.

In some embodiments, to position the three-dimensional model of the tibial insert in the three-dimensional anatomical image based on the positioning criteria may include to position the three-dimensional model of the tibial insert in the three-dimensional anatomical image such that the dwell point of the medial articular surface of the tibial insert is aligned with the dwell point of the medial tibial plateau of the patient's tibia included in the three-dimensional anatomical image.

Additionally, in some embodiments, to position the three-dimensional model of the femoral component in the three-dimensional anatomical image based on the positioning criteria may include to position the three-dimensional model of the femoral component in the three-dimensional anatomical image such that a center of a constant radius of curvature that defines an articular surface of the medial condyle of the femoral component is offset from an anatomical center of the medial epicondyle of the patient's femur included in the three-dimensional anatomical image by a reference amount.

Furthermore, in some embodiments, to position the three-dimensional model of the femoral component in the three-dimensional anatomical image based on the positioning criteria may include to position the three-dimensional model of the femoral component in the three-dimensional anatomical image such that an articular surface of the medial condyle of the femoral component that is defined by a constant radius of curvature is aligned with a posterior articular surface of the medial condyle of the patient's femur included in the three-dimensional anatomical image.

Additionally, to position the three-dimensional model of the femoral component in the three-dimensional anatomical image based on the positioning criteria may include to position the three-dimensional model of the femoral component in the three-dimensional anatomical image such that an articular surface of the medial condyle of the femoral component that is defined by a constant radius of curvature is aligned with an anterior articular surface of the medial condyle of the patient's femur included in the three-dimensional anatomical image.

In some embodiments, to position the three-dimensional model of the femoral component in the three-dimensional anatomical image based on the positioning criteria may include to position the three-dimensional model of the femoral component in the three-dimensional anatomical image such that an articular surface of a patellofemoral surface of the femoral component is aligned with a patellofemoral surface of the patient's femur included in the three-dimensional anatomical image.

Additionally, in some embodiments, to position the three-dimensional model of the femoral component in the three-dimensional anatomical image based on the positioning criteria may include to position the three-dimensional model of the femoral component in the three-dimensional anatomical image such that a center of a constant radius of curvature that defines an articular surface of a lateral condyle of the femoral component is offset from an anatomical center of the lateral epicondyle of the patient's femur included in the three-dimensional anatomical image by a reference amount.

The plurality of instructions, when executed, may further cause the surgical planning computing system to generate positioning data that defines orthopaedic coordinates at which the feature of the orthopaedic prosthesis should be located on a bone of the patient's anatomy.

Accordingly to an additional aspect of the present disclosure, a method for performing an orthopaedic surgery on a patient may include obtaining a three-dimensional anatomical image of a patient's bony anatomy in which medial pivoting orthopaedic prosthesis is to be implanted during the orthopaedic surgery. The three-dimensional anatomical image may include a three-dimensional image of a tibia and corresponding femur of the patient.

Additionally, the method may include operating a surgical planning computing system to (i) identify a dwell point of a medial tibial plateau of the patient's tibia in the three-dimensional anatomical image, (ii) identify a center of rotation of a medial condyle of the patient's femur in the three-dimensional anatomical image, (iii) determine positioning criteria for the medial pivoting orthopaedic prosthesis, wherein the medial pivoting orthopaedic prosthesis includes a tibial insert and a femoral component and wherein the positioning criteria identifies (a) an alignment between the dwell point of the medial articular surface of the tibial insert and the dwell point of the medial tibial plateau of the patient's tibia and (b) an alignment of a feature of a medial condyle of the femoral component based on the center of rotation of the medial condyle of the patient's femur, and (iv) position a three-dimensional model of the tibial insert and of the femoral component in the three-dimensional anatomical image based on the positioning criteria to generate an updated three-dimensional anatomical image that includes the three-dimensional model of the orthopaedic prosthesis. The method may also include performing the orthopaedic surgery to implant the orthopaedic prosthesis into the patient's bone using the updated three-dimensional anatomical image as a surgical plan for the orthopaedic surgery.

In some embodiments, to position the three-dimensional model of the tibial insert in the three-dimensional anatomical image based on the positioning criteria may include to position the three-dimensional model of the tibial insert in the three-dimensional anatomical image such that the dwell point of the medial articular surface of the tibial insert is aligned with the dwell point of the medial tibial plateau of the patient's tibia included in the three-dimensional anatomical image.

Additionally, in some embodiments, to position the three-dimensional model of the femoral component in the three-dimensional anatomical image based on the positioning criteria may include to position the three-dimensional model of the femoral component in the three-dimensional anatomical image such that a center of a constant radius of curvature that defines an articular surface of the medial condyle of the femoral component is offset from an anatomical center of the medial epicondyle of the patient's femur included in the three-dimensional anatomical image by a reference amount.

Furthermore, in some embodiments, to position the three-dimensional model of the femoral component in the three-dimensional anatomical image based on the positioning criteria may include to position the three-dimensional model of the femoral component in the three-dimensional anatomical image such that an articular surface of the medial condyle of the femoral component that is defined by a constant radius of curvature is aligned with a posterior articular surface of the medial condyle of the patient's femur included in the three-dimensional anatomical image.

Additionally, to position the three-dimensional model of the femoral component in the three-dimensional anatomical image based on the positioning criteria may include to position the three-dimensional model of the femoral component in the three-dimensional anatomical image such that an articular surface of the medial condyle of the femoral component that is defined by a constant radius of curvature is aligned with an anterior articular surface of the medial condyle of the patient's femur included in the three-dimensional anatomical image.

In some embodiments, to position the three-dimensional model of the femoral component in the three-dimensional anatomical image based on the positioning criteria may include to position the three-dimensional model of the femoral component in the three-dimensional anatomical image such that an articular surface of a patellofemoral surface of the femoral component is aligned with a patellofemoral surface of the patient's femur included in the three-dimensional anatomical image.

Additionally, in some embodiments, to position the three-dimensional model of the femoral component in the three-dimensional anatomical image based on the positioning criteria may include to position the three-dimensional model of the femoral component in the three-dimensional anatomical image such that a center of a constant radius of curvature that defines an articular surface of a lateral condyle of the femoral component is offset from an anatomical center of the lateral epicondyle of the patient's femur included in the three-dimensional anatomical image by a reference amount.

According to yet a further aspect of the present disclosure, one or more non-transitory, machine-readable storage media comprising a plurality of instructions stored thereon that, in response to execution by a computing system, cause the computing system to identify a dwell point of a medial tibial plateau of a patient's tibia captured in a three-dimensional anatomical image of the patient's bony anatomy and identify a center of rotation of a medial condyle of a patient's femur a captured in the three-dimensional anatomical image. The plurality of instructions, when executed may further cause the computing system to determine positioning criteria for a medial pivoting orthopaedic prosthesis that is to be used in the orthopaedic surgical procedure. The medial pivoting orthopaedic prosthesis may include a tibial insert and a femoral component. Additionally, the positioning criteria may identify (i) an alignment between the dwell point of the medial articular surface of the tibial insert and the dwell point of the medial tibial plateau of the patient's tibia and (ii) an alignment of a feature of a medial condyle of the femoral component based on the center of rotation of the medial condyle of the patient's femur.

The plurality of instructions, when executed may further cause the computing system to position a three-dimensional model of the tibial insert and of the femoral component in the three-dimensional anatomical image based on the positioning criteria to generate an updated three-dimensional anatomical image that includes the three-dimensional model of the orthopaedic prosthesis. Additionally, the plurality of instructions, when executed, may cause the surgical planning computing system to display the updated three-dimensional anatomical image.

In some embodiments, to position the three-dimensional model of the tibial insert in the three-dimensional anatomical image based on the positioning criteria may include to position the three-dimensional model of the tibial insert in the three-dimensional anatomical image such that the dwell point of the medial articular surface of the tibial insert is aligned with the dwell point of the medial tibial plateau of the patient's tibia included in the three-dimensional anatomical image.

Additionally, in some embodiments, to position the three-dimensional model of the femoral component in the three-dimensional anatomical image based on the positioning criteria may include to position the three-dimensional model of the femoral component in the three-dimensional anatomical image such that a center of a constant radius of curvature that defines an articular surface of the medial condyle of the femoral component is offset from an anatomical center of the medial epicondyle of the patient's femur included in the three-dimensional anatomical image by a reference amount.

Furthermore, in some embodiments, to position the three-dimensional model of the femoral component in the three-dimensional anatomical image based on the positioning criteria may include to position the three-dimensional model of the femoral component in the three-dimensional anatomical image such that an articular surface of the medial condyle of the femoral component that is defined by a constant radius of curvature is aligned with a posterior articular surface of the medial condyle of the patient's femur included in the three-dimensional anatomical image.

Additionally, to position the three-dimensional model of the femoral component in the three-dimensional anatomical image based on the positioning criteria may include to position the three-dimensional model of the femoral component in the three-dimensional anatomical image such that an articular surface of the medial condyle of the femoral component that is defined by a constant radius of curvature is aligned with an anterior articular surface of the medial condyle of the patient's femur included in the three-dimensional anatomical image.

In some embodiments, to position the three-dimensional model of the femoral component in the three-dimensional anatomical image based on the positioning criteria may include to position the three-dimensional model of the femoral component in the three-dimensional anatomical image such that an articular surface of a patellofemoral surface of the femoral component is aligned with a patellofemoral surface of the patient's femur included in the three-dimensional anatomical image.

Additionally, in some embodiments, to position the three-dimensional model of the femoral component in the three-dimensional anatomical image based on the positioning criteria may include to position the three-dimensional model of the femoral component in the three-dimensional anatomical image such that a center of a constant radius of curvature that defines an articular surface of a lateral condyle of the femoral component is offset from an anatomical center of the lateral epicondyle of the patient's femur included in the three-dimensional anatomical image by a reference amount.

BRIEF DESCRIPTION OF THE DRAWINGS

The detailed description particularly refers to the following figures, in which.

DETAILED DESCRIPTION OF THE DRAWINGS

Figure 1:
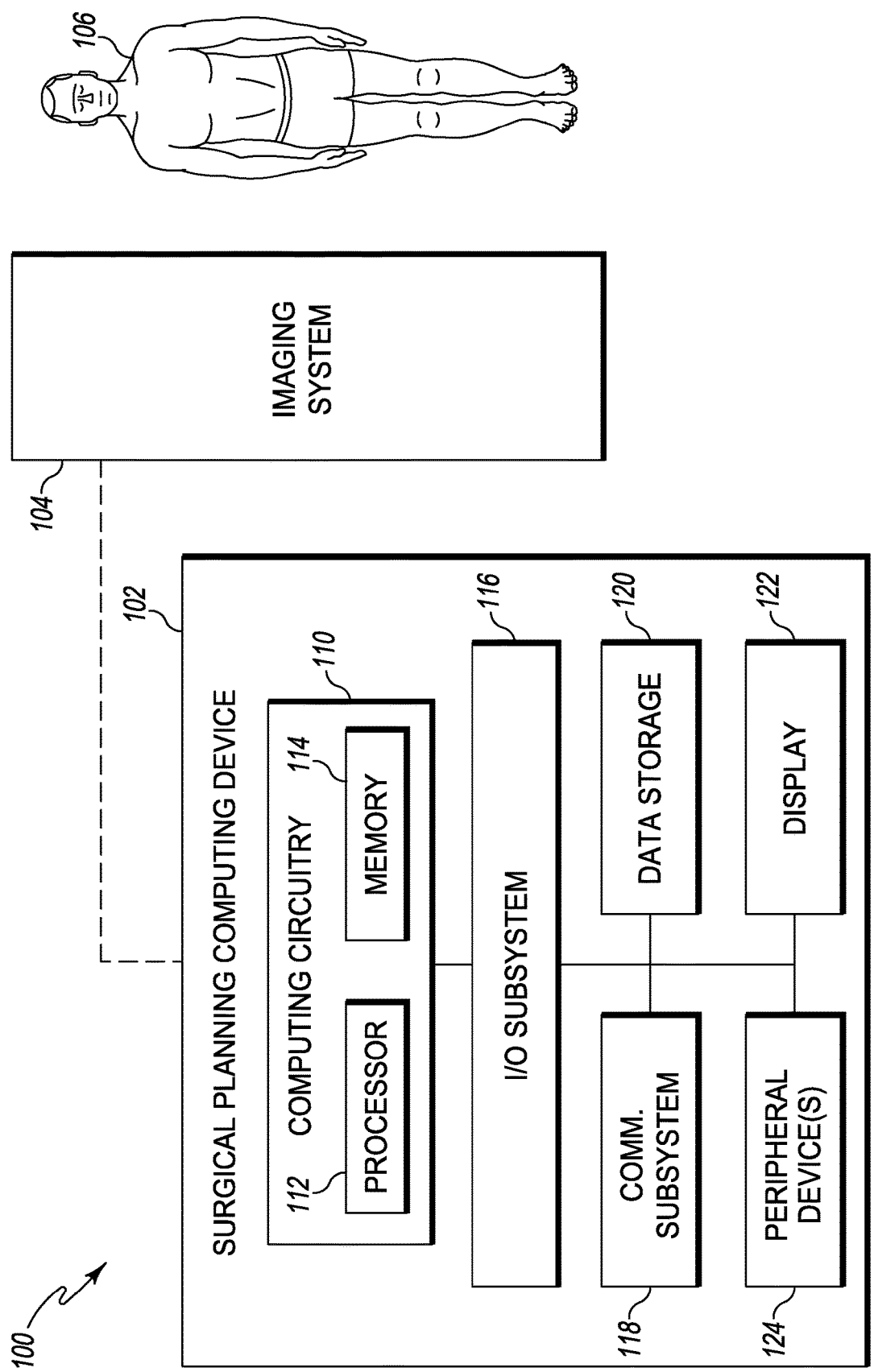
FIG. 1 is a block diagram of a surgical planning computing system for generating a surgical plan for an orthopaedic surgical procedure.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. While the disclosure below describes techniques and instrument system in reference to a patient's tibia, it should be appreciated that all of the systems and techniques described below may be used to surgically prepare other bones, such as, for example, a distal end of a patient's femur.

Referring now to FIG. 1, an illustrative surgical planning computing system 100 for generating a surgical plan for an orthopaedic surgical procedure includes a surgical planning computing device 102 and an imaging system 104. In use, the imaging system 104 is configured to generate medical images, such as two-dimensional or three-dimensional medical images, of the bony anatomy of a patient 106. In those embodiments in which the medical images are two-dimensional, the surgical planning computing device 102 is configured to convert the two-dimensional images to a three-dimensional image(s) and analyze the generated (or obtained) three-dimensional image of the patent's bony anatomy to properly position a three-dimensional model of an orthopaedic prosthesis into the three-dimensional image based on corresponding positioning criteria. As discussed in more detail below, the positioning criteria may identify a particular alignment of an anatomical landmark of the patient's bony anatomy and a corresponding feature of the orthopaedic prosthesis that is to be implanted into the patient.

It should be appreciated that the positioning criteria may differ based on several factors, including the type of orthopaedic prosthesis that is to be used in the orthopaedic surgical procedure. In particular, orthopaedic prostheses designed to allow or facilitate "medial pivoting" may perform better in a different position on the patient's bony anatomy relative to a non-medial pivoting orthopaedic prosthesis.

Figure 2:
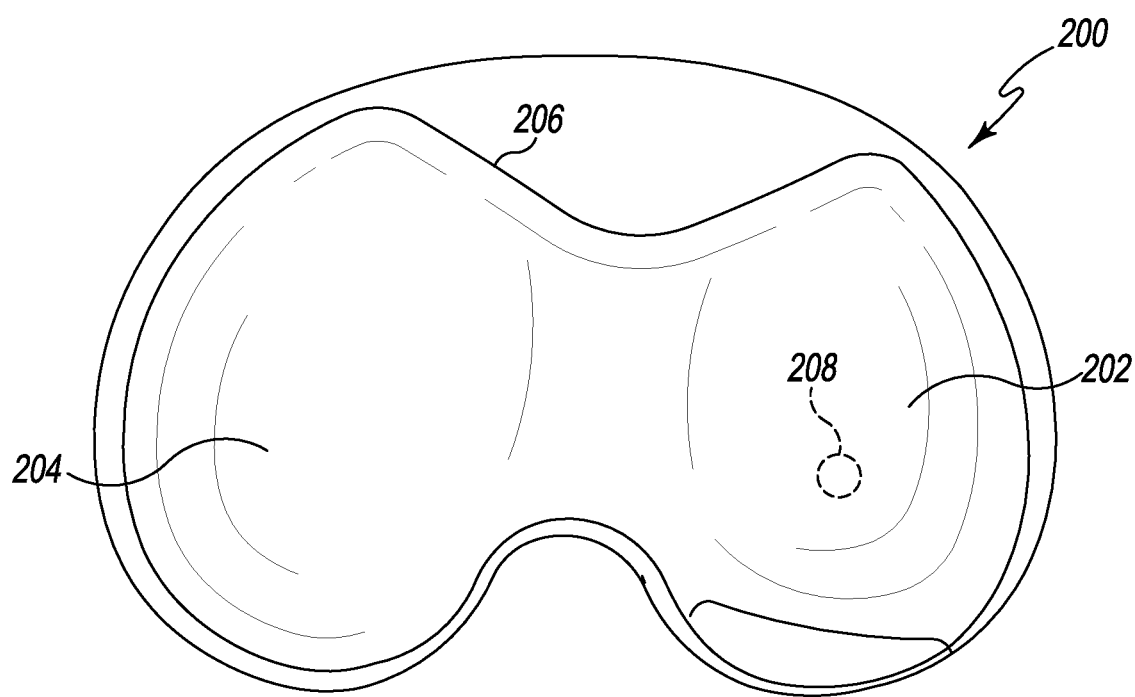
FIG. 2 is a plan view of an embodiment of a tibial component that may be used in the surgical plan generated by the surgical planning computing system of FIG. 1.
Figure 3:
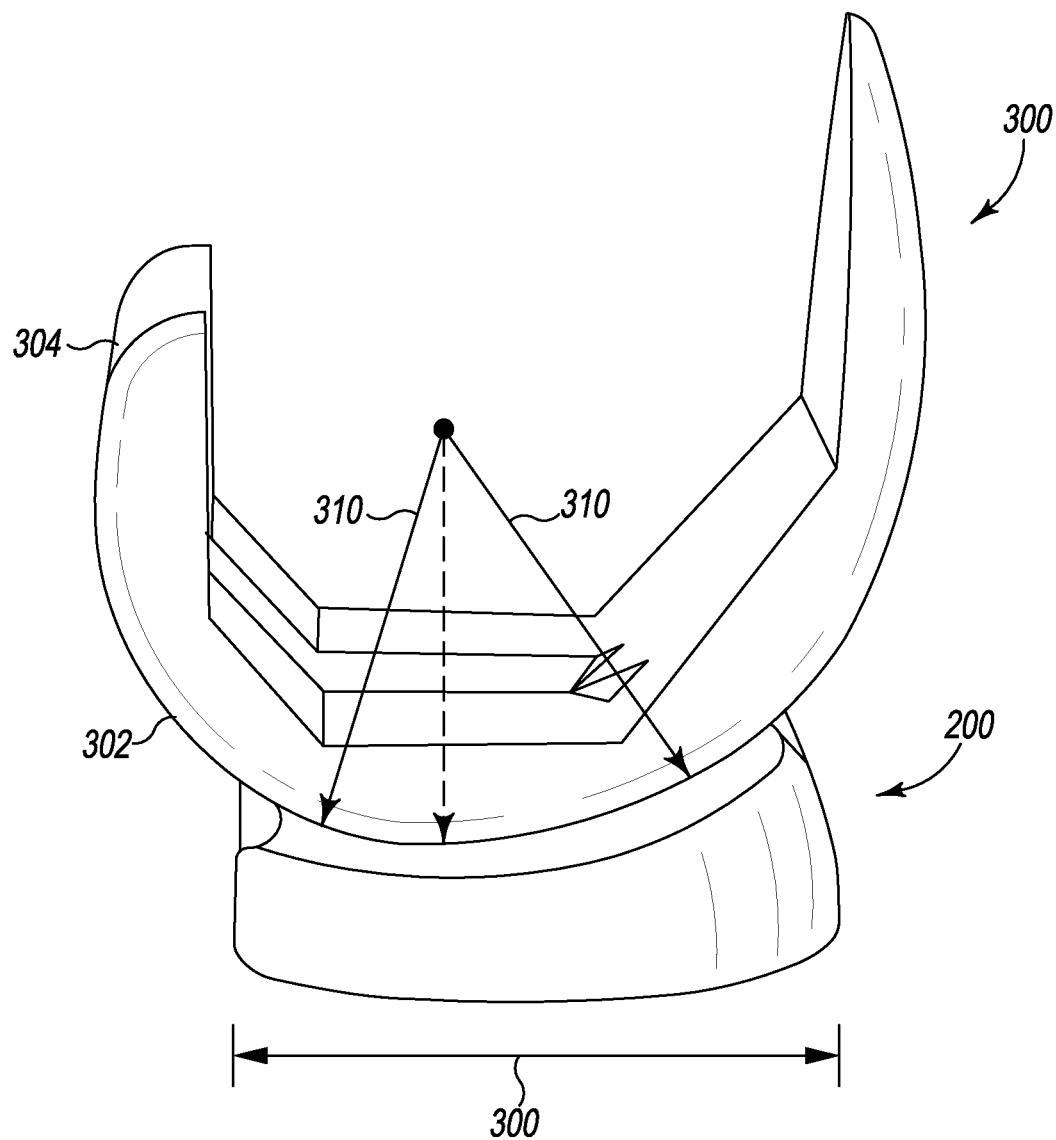
FIG. 3 is a perspective side view of an embodiment of a femoral component that may be used in the surgical plan generated by the surgical planning computing system of FIG. 1.

For example, the illustrative surgical planning computing system 100 may be used to generate a surgical plan for the implantation of a medial pivoting orthopaedic prosthesis including a tibial insert 200, as shown in FIG. 2, and a femoral component 300, as shown in FIG. 3. The illustrative tibial insert 200 includes a medial articular surface 202 and a lateral articular surface 204. The articular surfaces 202, 204 are, however, asymmetrically-shaped to provide asymmetric pivoting of the femoral component 300 (bearing on the tibial insert 200. The medial articular surface 202 of the tibial insert 200 is more conforming to, for example, a condylar portion of the femoral component 300 than a typical non-medial-pivot-designed tibial insert. The tibial insert 200 also has a relatively raised anterior surface (anterior medial lip height 206) on a medial side of the tibial insert 200, compared to a typical non-medial-pivot-designed tibial insert. Furthermore, with respect to a typical non-medial-pivot-designed tibial insert, the dwell point 208 of the medial articular surface 202 is positioned more posteriorly. For example, the dwell point 208 is typically positioned in the posterior third of the anterior-posterior (AP) dimension of the tibial insert 200.

Referring now to FIG. 3, the illustrative surgical planning computing system 100 may be also be used to generate a surgical plan for the implantation of a medial-pivot-designed femoral component 300, which may be used in conjunction with the tibial insert 200. The illustrative femoral component 300 includes a medial femoral condyle 302 configured to articulate on the medial articular surface 202 of the tibial insert 200 and a lateral femoral condyle 304 configured to articulate on the lateral articular surface 204. One or both of the femoral condyles 302, 304 may include a femoral articular surface that is defined by a constant radius of curvature 310. Depending on the particular design, the constant radius of curvature 310 may extend anteriorly to a degree of hyperextension between 10 and 30 degrees (e.g., −20 degrees of flexion) and extend posteriorly to a degree of flexion of between 30 and 70 degrees (e.g., 50 degrees). Of course, the constant radius of curvature 310 may extend across a different range of degrees in other embodiments. In some embodiments, the constant radius of curvature 310 may be followed, posteriorly, by gradually decreasing radii of curvature that define the remainder of a sagittal shape of the femoral component 300.

For a natural medial pivoting motion, some embodiments of the tibial insert 200 and femoral component 300 may include a higher conformity on the medial interface relative to the lateral interface. For example, the anterior-posterior surface conformity of the medial articular surface 202 of the tibial insert and the femoral articular surface of the medial condyle 302 of the femoral component 300 may have a conformity of 96% or greater. Additionally, the medial-lateral conformity of the medial articular surface 202 and the femoral articular surface of the medial condyle 302 may be 93% or greater.

The above-described features of a medial pivoting orthopaedic prosthesis may dictate different positioning criteria relative to a non-medial pivot design. For example, it has been determined that improved joint movement is obtained by positioning the tibial insert 200 in alignment with the patient's existing medial collateral ligament. To do so, in the illustrative embodiment, the tibial insert 200 is positioned relative to the patient's bony anatomy such that the dwell point 208 of the medial articular surface 202 of the tibial insert 200 is aligned with (e.g., congruent with) the dwell point of the medial tibial plateau of the patient's tibia. Such positioning may place the tibial insert 200 in a position such that the dwell point 208 approximates a location of the medial collateral ligament inserts to the patient's medial tibial plateau. In this way, the tibial insert 200 is located in a more natural position relative to the patient's medial collateral ligament. The lateral side of the tibial insert 200 may be allowed to float and positioned during the surgical procedure using a lateral float position (i.e., positioning the lateral side based on the flexion and extension motion of the patient's knee) as discussed in more detail below.

With regard to the positioning of the femoral component 300, it has been determined that improved joint movement is obtained by positioning the femoral component 300 in alignment with the center of rotation of the patient's medial condyle. To do so, in some embodiments, the femoral component 300 may be positioned relative to the patient's bony anatomy such that center or origin of the constant radius of curvature 310 of the femoral component 300 is offset from an anatomical center of the medial (and/or lateral) epicondyle of the patient's femur by a reference amount such, as, for example, 5-10 millimeters. Additionally or alternatively, in some embodiments, the femoral component 300 may be positioned relative to the patient's bony anatomy such that the femoral articular surface of the femoral component 300 defined by the constant radius of curvature 310 is aligned with (e.g., congruent with) the posterior articular surface of a medial condyle of the patient's femur or with the anterior articular surface of the medial condyle of the patient's femur. Further, in some embodiments, the femoral component 300 may be positioned relative to the patient's bony anatomy such that an articular surface of the patellofemoral surface of the femoral component 300 is aligned (e.g., congruent with) the patellofemoral surface of the patient's femur. The lateral femoral condyle of the femoral component 300 may be allowed to float, similar to the lateral side of the tibial insert 200 as discussed in more detail below. As such, by properly placing the articular surface conformity between the tibial insert 200 and the femoral component 300, a more normal motion of the prosthetic knee may be achieved.

Referring back to FIG. 1, the surgical planning computing device 102 may be embodied as any type of computing device capable of generating a surgical plan and performing the functions described herein. For example, the surgical planning computing device 102 may be embodied as any type of computer or computing device such as a desktop computer, a server, a mobile computing device, a laptop computer, a tablet computer, a "smart" phone, an appliance device, a digital assistant, or other computing device capable of performing the functions described herein. The surgical planning computing device 102 includes computing circuitry 110, an input/output ("I/O") subsystem 116, a communication subsystem 118, a data storage 120, a display 122 and, in some cases, one or more peripheral devices 124. Of course, it should be appreciated that the communication subsystem 212 may include other or additional components, such as those commonly found in a typical computing device or server, in other embodiments. Additionally, in some embodiments, one or more of the illustrative components may be incorporated in, or otherwise form a portion of, another component.

The computing circuitry 110 may be embodied as any type of device or collection of devices capable of performing various computing functions. In some embodiments, the computing circuitry 110 may be embodied as a single device such as an integrated circuit, an embedded system, a field-programmable-array (FPGA, a system-on-a-chip (SOC), or other integrated system or device. Additionally, in some embodiments, the computing circuitry 110 includes, or is embodied as, a processor 112 and memory 114. The processor 112 may be embodied as any type of processor capable of performing the functions described herein. For example, the processor 112 may be embodied as a single or multi-core processor(s), digital signal processor, microcontroller, or other processor or processing/controlling circuit. Similarly, the memory 114 may be embodied as any type of volatile or non-volatile memory or data storage capable of performing the functions described herein.

The computing circuitry 110 is communicatively coupled to other components of the surgical planning computing device 102 via the I/O subsystem 116, which may be embodied as circuitry and/or components to facilitate input/output operations with computing circuitry 110 (e.g., with the processor 112 and/or memory 114) and other components of the surgical planning computing device 102. For example, the I/O subsystem 116 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 116 may be incorporated, along with the processor 112, the memory 114, and other components of the surgical planning computing device 102, into the computing circuitry 110.

The communication subsystem 118 may be embodied as any type of communication circuit, device, or collection thereof, capable of enabling communications between the surgical planning computing device 102 and other components of the system 100, such as the imaging system 104. To do so, the communication subsystem 118 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The data storage 120 may be embodied as any type of device or devices configured for short-term or long-term storage of data such as, for example, memory devices and circuits, memory cards, hard disk drives, solid-state drives, or other data storage devices. As discussed in more detail below, the data storage 120 may store two-dimensional images of the bony anatomy of the patient 106 generated by the imaging system 104, as well three-dimensional images generated from those two-dimensional images. Additionally, the data storage 120 may store positioning criteria for various orthopaedic prostheses, which defines a particular alignment of an anatomical landmark of the patient's bony anatomy and a corresponding feature of the orthopaedic prosthesis that is to be implanted into the patient as discussed above.

The display 122 may be embodied as any type of display capable of displaying digital information, such as a liquid crystal display (LCD), a light emitting diode (LED) display, a plasma display, a cathode ray tube (CRT), or other type of display device. In some embodiments, the display 122 may include, or be incorporated with, a touch screen to facilitate touch input to the surgical planning computing device 102. Additionally, in some embodiments, the surgical planning computing device 102 may include one or more peripheral devices 124. Such peripheral devices 124 may include any type of peripheral device commonly found in a computing device or server such as audio input devices, other input/output devices, interface devices, and/or other peripheral devices.

The imaging system 104 may be embodied as any type of imaging device or collection of devices capable of generating two-dimensional or three-dimensional digital anatomical images of the bony anatomy of the patient 106. For example, the imaging system 104 may utilize X-ray, magnetic resonance imaging (MRI), computed tomography (CT), fluoroscopy, and/or ultrasound to capture the digital anatomical images. In some embodiments, the imaging system 104 may be in communication with surgical planning computing device 102 over a suitable network, such as a wired or wireless network. Additionally, although illustrated as separate components in FIG. 1, the surgical planning computing device 102 and the imaging system 104 may be incorporated into a single device in other embodiments.

Although the surgical planning computing system 100 is illustrated in FIG. 1 and described above as a local computing device and system, it should be appreciated that the system 100 may be embodied as a cloud-based system. In such embodiments, the functions of the surgical planning computing device 102 may be performed by one or more servers or similar computing devices located remotely from the operating room environment. Additionally, it should be appreciated that although the surgical planning computing device 102 has been described as including particular components (e.g., the I/O subsystem, data storage, display, etc.), the surgical computing device 102 may be embodied as a more simplistic computing device (e.g., in a cloud-based system) or incorporated into another computing device or system in other embodiments.

Figure 4:
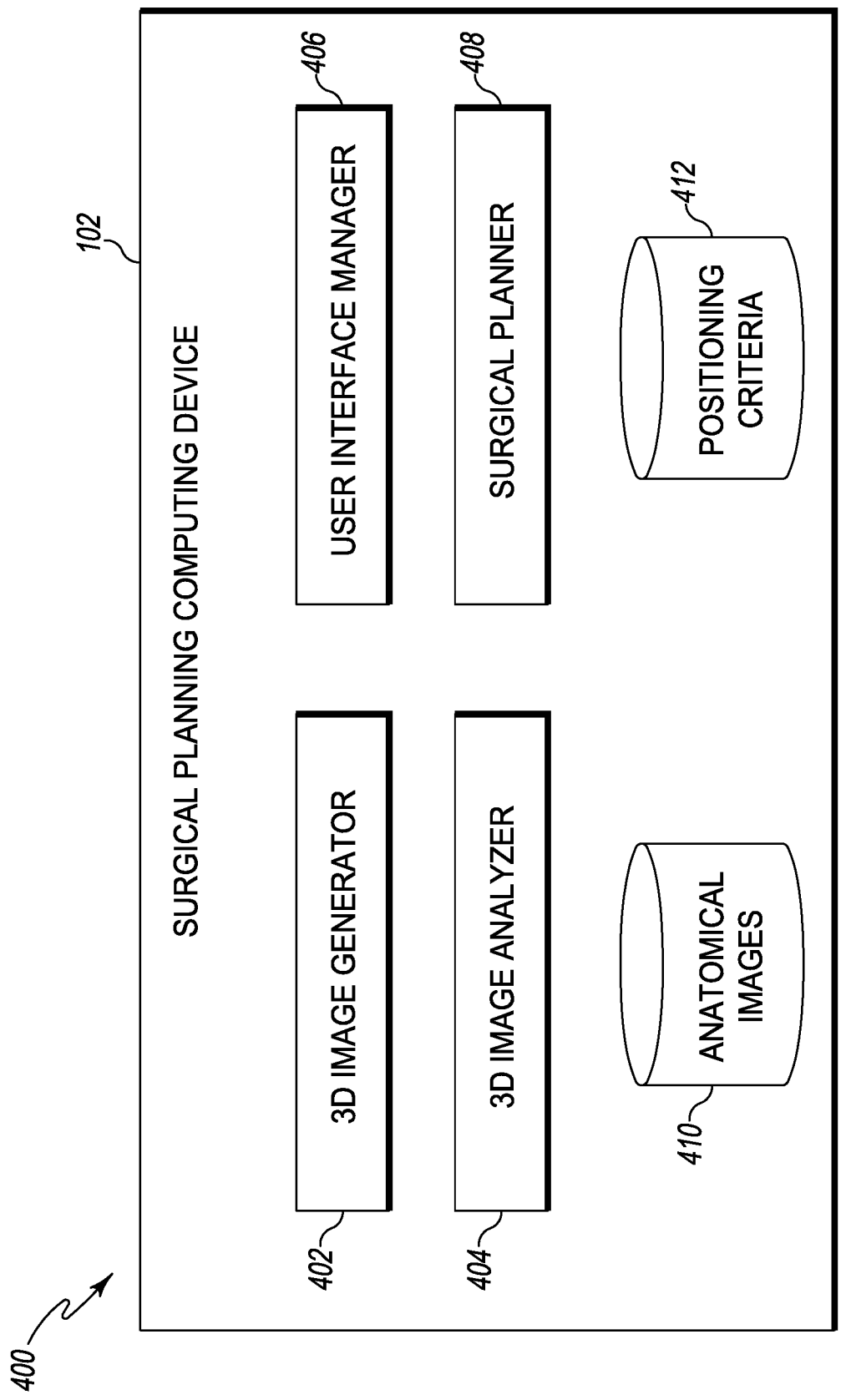
FIG. 4 is a block diagram of an environment that may be established by a surgical planning computing device of the system of FIG. 1.

Referring now to FIG. 4, the surgical planning computing device 102 may establish an environment 400 during operation. The illustrative environment 400 includes a 3D image generator 402, a 3D image analyzer 404, a user interface manager 406, and a surgical planner 408. Additionally, the environment 400 may include an anatomical images database 410 and/or a positioning criteria database 412. Each of the various components of the environment 400 may be embodied as hardware, firmware, software, or a combination thereof. As such, in some embodiments, one or more of the components of the environment 400 may be embodied as circuitry or collection of electrical devices (e.g., 3D image generator circuitry 402, 3D image analyzer circuitry 404, user interface manager circuitry 406, surgical planner circuitry 408, etc.). It should be appreciated that one or more functions described herein as being performed by the 3D image generator circuitry 402, the 3D image analyzer circuitry 404, user interface manager circuitry 406, and/or the surgical planner circuitry 408 may be performed, at least in part, by one or more other components of the surgical planning computing device 102, such as the computing circuitry 110, the I/O subsystem 116, the communication subsystem 118, an application specific integrated circuit (ASIC), a programmable circuit such as an field-programmable gate array (FPGA), and/or other components of the surgical planning computing device 102. It should be further appreciated that associated instructions may be stored in the memory 114, the data storage device(s) 120, and/or another data storage location, which may be executed by processor 112 of the computing circuitry 110 and/or other computational processor of the surgical planning computing device 102.

Additionally, in some embodiments, one or more of the illustrative components of the environment 400 may form a portion of another component and/or one or more of the illustrative components may be independent of one another. Furthermore, it should be appreciated that the environment 400 of the surgical planning computing device 102 may include other components, sub-components, modules, sub-modules, logic, sub-logic, and/or devices commonly found in a computing device (e.g., device drivers, interfaces, etc.), which are not illustrated in FIG. 1 or 4 for clarity of the description.

The 3D image generator 402 is configured to generate or otherwise obtain three-dimensional anatomical images. In those embodiments in which the imaging system 104 generated two-dimensional images, the 3D image generator 402 is configured to obtain the two-dimensional images from the imaging system 104 and convert two-dimensional anatomical images to three-dimensional anatomical images. To do so, the 3D image generator 402 may utilize any suitable two-dimensional-to-three-dimensional morphing algorithm. For example, any one or combination of the morphing algorithms disclosed in U.S. Pat. Nos. 4,791,934, 5,389,101, 6,701,174, U.S. Patent Application Publication No. US2005/0027492, U.S. Pat. Nos. 7,873,403, 7,570,791, PCT Patent No. WO99/59106, European Patent No. EP1348394A1, and/or European Patent No. EP1498851A1 may be used. Of course, in embodiments in which the imaging system 104 generates three-dimensional anatomical images natively, the 3D image generator 402 may be tasked with obtaining those three-dimensional anatomical images from the imaging system 104. The 3D image generator 402 may store the two-dimensional anatomical images and/or three-dimensional anatomical images in the anatomical images database 410.

The 3D image analyzer 404 is configured to analyze the three-dimensional anatomical images of the patient's bony anatomy generated by the 3D image generator (or natively by the imaging system 104) to identify one or more anatomical landmarks of the patient's bony anatomy captured in the three-dimensional anatomical images. To do so, the 3D image analyzer 404 may utilize any suitable feature detection algorithm to identify the desired anatomical landmarks in the three-dimensional anatomical images. The particular anatomical landmarks and number of landmarks identified by the 3D image analyzer 404 may be dependent on various criteria including, for example, the particular type of orthopaedic prosthesis being used, the surgeon's preferences, the patient's existing bony anatomy, and/or other criteria. For example, in the illustrative embodiment, the 3D image analyzer 404 may be configured to identify the dwell point of a tibial plateau of a tibia of the patient 106, the anatomical center of the medial epicondyle of the femur of the patient 106, the posterior articular surface of a condyle of a femur of the patient 106, the anterior articular surface of a condyle of the femur of the patient 106, the articular surface of the patellofemoral surface of the femur of the patient 106, and/or the anatomical center of the lateral epicondyle of the femur of the patient 106 captured in the three-dimensional image.

As discussed in more detail below, in some embodiments, the orthopaedic surgeon may provide input to the surgical planning computing device 102 to facilitate or supplement the identification of the one or more anatomical landmarks of the patient's bony anatomy captured in the three-dimensional anatomical images. To do so, for example, the orthopaedic surgeon may manually annotate the three-dimensional anatomical images to indicate particular anatomical landmarks to be considered by the surgical planning computing device 102.

The user interface manager 406 is configured to present and manage input/output of the surgical planning computing device 102. For example, the user interface manager 406 may control the display 122 to present a graphical user interface with which an orthopaedic surgeon may interact. In the illustrative embodiment, for example, the orthopaedic surgeon selects the orthopaedic prosthesis and the particular positioning criteria that is to be used in the orthopaedic surgical procedure, which may be stored in the positioning criteria database 412. Additionally, the user interface manager 406 displays the determined surgical plan, which includes an updated three-dimensional anatomical image of the patient's bony anatomy including a three-dimensional model of the selected orthopaedic prosthesis positioned therein based on the selected positioning criteria as discussed in more detail below.

The surgical planner 408 is configured to generate a surgical plan, or portion thereof, for the corresponding orthopaedic surgical procedure. To do so, the surgical planner 408 positions (e.g., overlay or otherwise incorporate) a three-dimensional model of the selected orthopaedic prosthesis in the three-dimensional image in a location that is based the positioning criteria, which may be selected by the orthopaedic surgeon as discussed above or otherwise determined by the surgical planning computing device 102 based on the orthopaedic prosthesis, the particular bone of the patient being operated on, and/or other considerations. For example, the surgical planner 408 may position the three-dimensional model of the orthopaedic prosthesis in the three-dimensional anatomical image such that one or more positioning criterion is satisfied. As discussed above, the positioning criteria may define a particular alignment of an anatomical landmark of the patient's bony anatomy as identified by the 3D image analyzer with a particular feature of the orthopaedic prosthesis as represented by the three-dimensional model. As discussed further below, the surgical planner 408 may be configured generate multiple surgical plans, each including the orthopaedic prosthesis in different locations, for consideration by the orthopaedic surgeon.

Figure 5A:
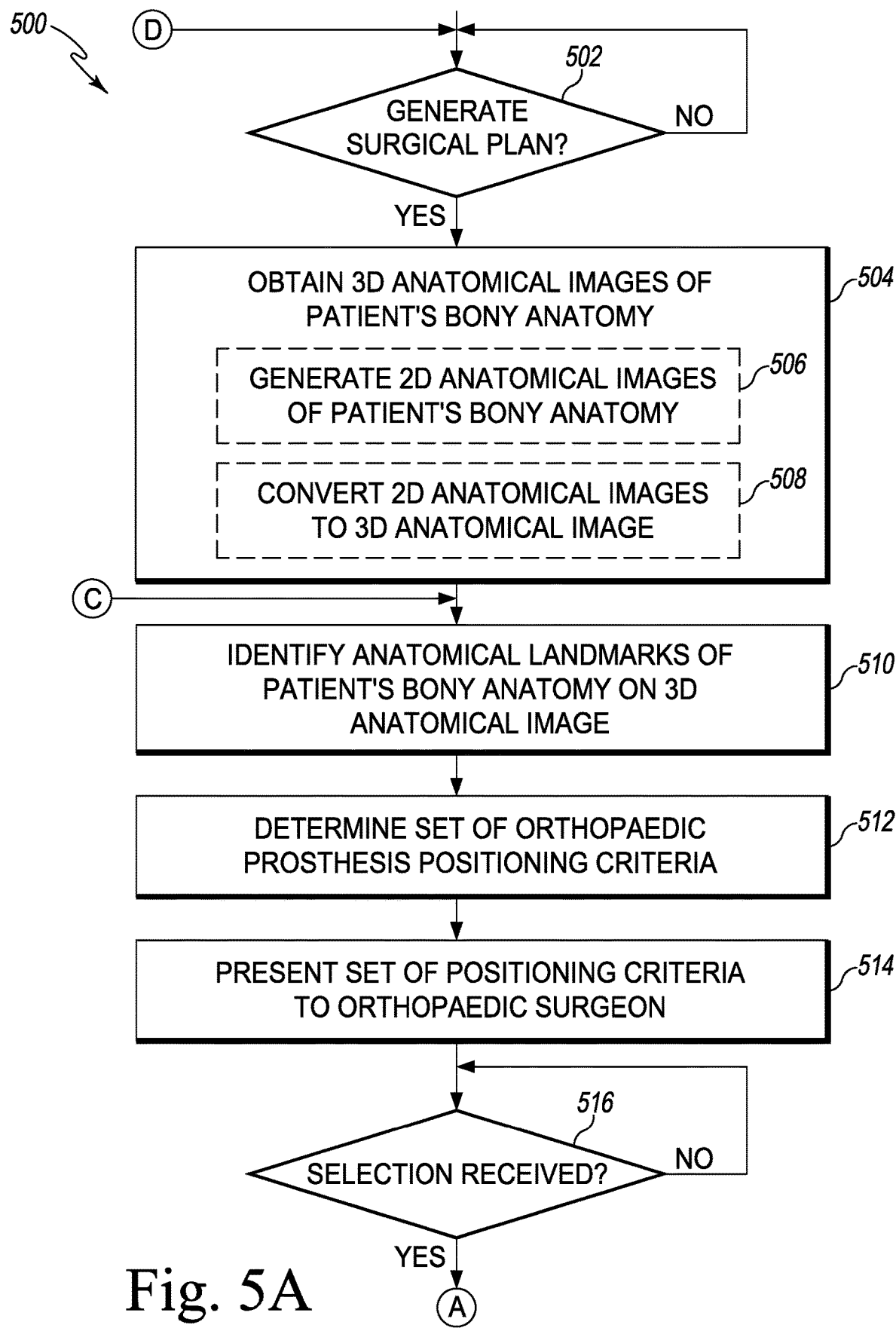
FIGS. 5A-5D are a flow diagram of a method for generating a surgical plan, which may be executed by the surgical planning computing device of the system of FIG. 1.
Figure 5B:
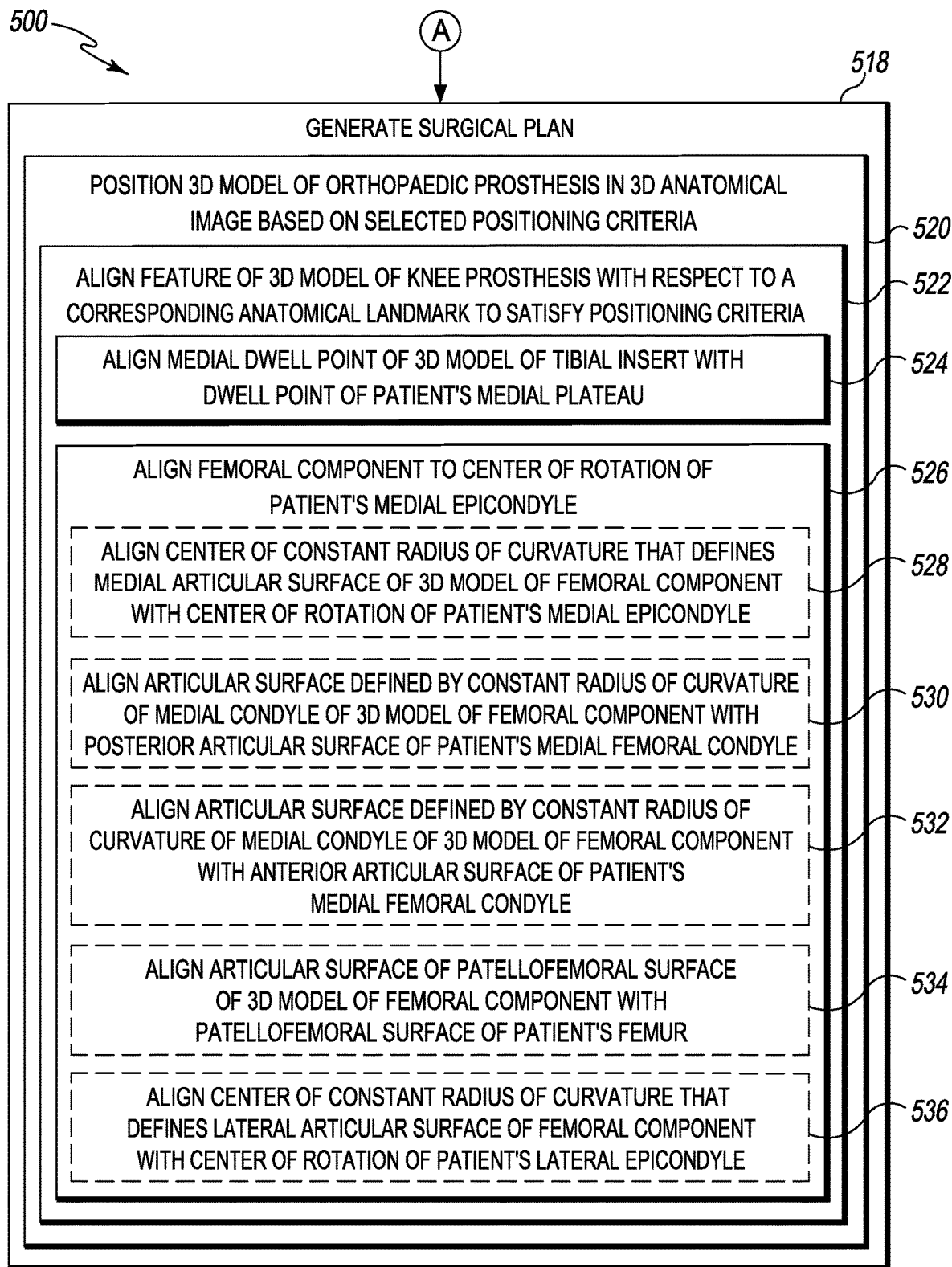
Figure 5C:
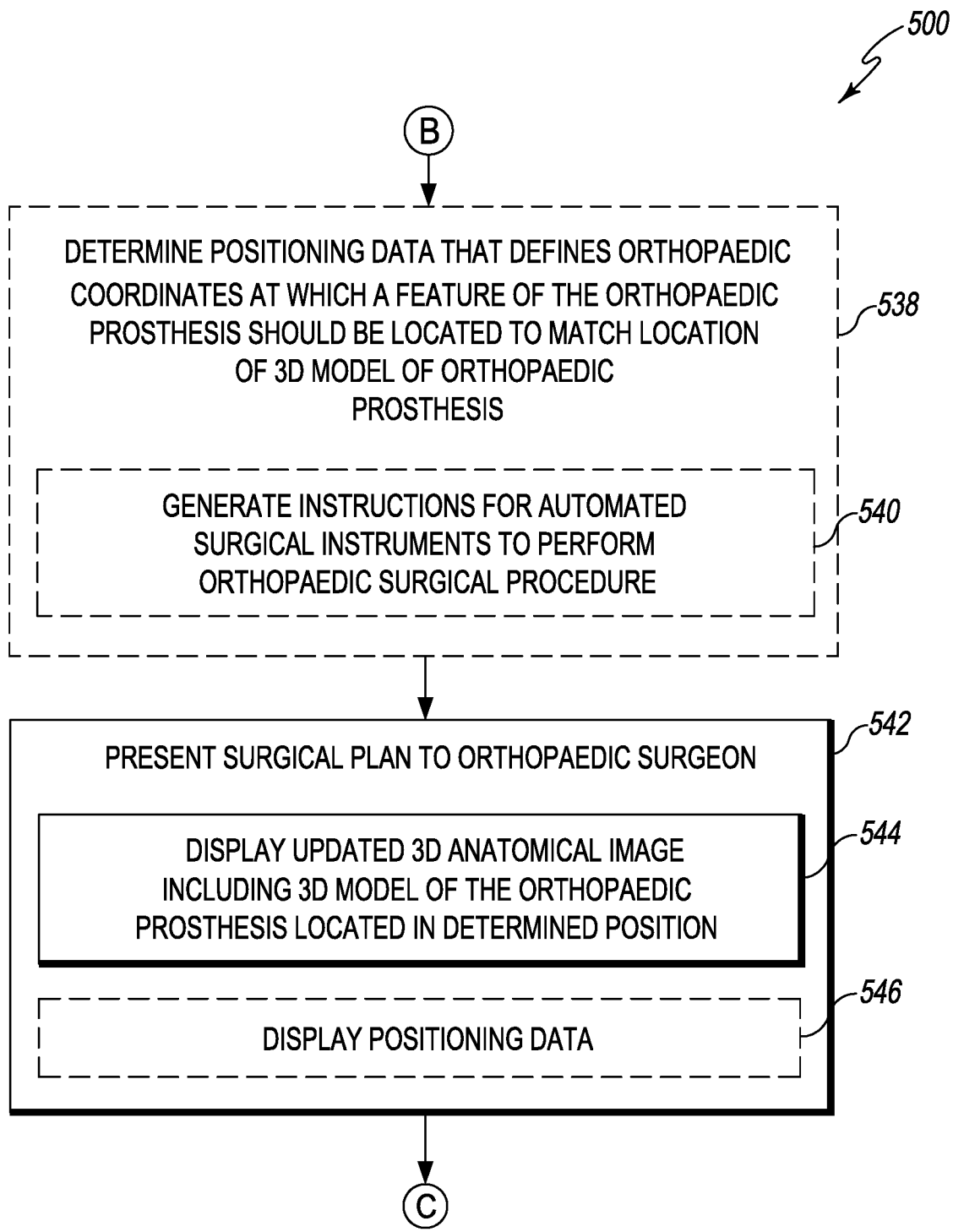

Referring now to FIGS. 5A-5C, in use, the surgical planning computing device 102 may perform a method 500 for generating a surgical plan for an orthopaedic surgical procedure. The method 500, or portions thereof, may be embodied as instructions executable by the processor 112 and stored in, for example, the memory 114. Additionally, the instructions embodying the method 500 may be stored on any suitable non-transitory storage media.

The method 500 begins with block 502 in which the surgical planning computing device 102 determines whether to generate a surgical plan. For example, the surgical planning computing device 102 may await input from an orthopaedic surgeon, such as a selection of an orthopaedic prosthesis to be implanted, to begin the execution of the method 500.

If the surgical planning computing device 102 determines to generate a surgical plan, the method 500 advances to block 504 in which the surgical planning computing device 102 obtains three-dimensional anatomical images of the relevant bony anatomy of the patient (i.e., the bone or bones that will be operated on). In embodiments in which the imaging system 104 is incorporated in the surgical planning computing device 102, the surgical planning computing device 102 may generate two-dimensional anatomical images of the patient's bony anatomy in block 506. Alternatively, the surgical planning computing device 102 may obtain two-dimensional anatomical images of the patient's bony anatomy from the imaging system 104 via, for example, a suitable communication link (e.g., over a network). Regardless, if the images obtained from the imaging system 104 are not three-dimensional, the surgical planning computing device 102 converts the two-dimensional anatomical images to a three-dimensional anatomical image in block 508. To do so, as discussed above, the surgical planning computing device 102 may utilize any suitable two-dimensional-to-three-dimensional morphing algorithm. In embodiments in which the imaging system 104 generates three-dimensional images natively, the surgical planning computing device 102 may simply obtain those three-dimensional images from the imaging system 104 without the need to convert the obtained images.

Figure 6:
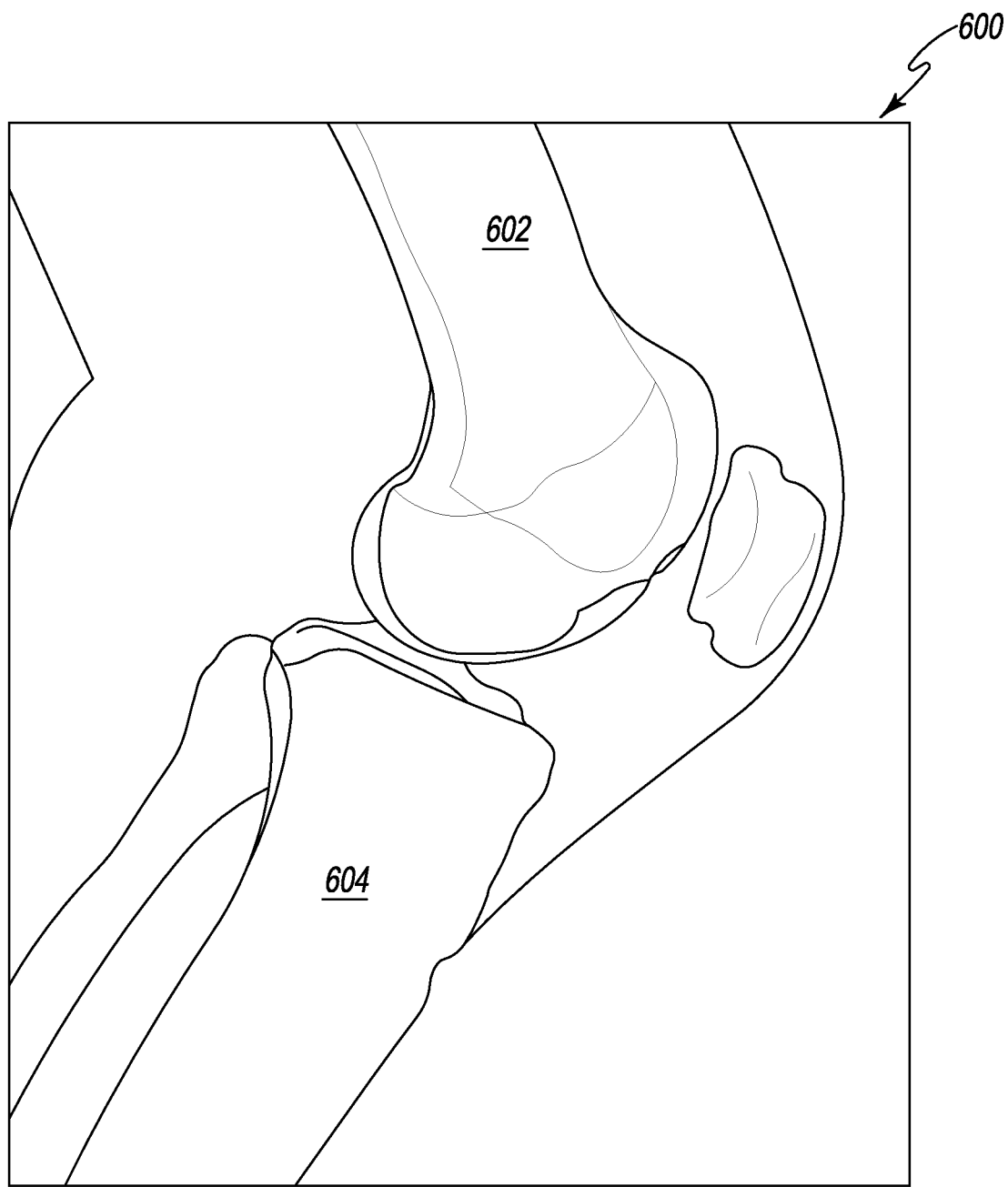
FIG. 6 is an illustration of a three-dimensional image of a patient's boney anatomy.

An illustrative three-dimensional anatomical image 600 that may be obtained or generated by the surgical planning computing device is illustrated in two-dimensions in FIG. 6. The illustrative three-dimensional anatomical image 600 includes a femur 602 and tibia 604 of the patient 106.

Referring back to FIG. 5A, in block 510, the surgical planning computing device 102 identifies one or more anatomical landmarks on the patient's boney anatomy in the three-dimensional anatomical image. To do so, the surgical planning computing device 102 may utilize any suitable feature detection algorithm to identify the desired anatomical landmarks in the three-dimensional anatomical images. As discussed above, the particular anatomical landmarks and number of landmarks identified by the surgical planning computing device 102 may be dependent on various criteria including, for example, the particular type of orthopaedic prosthesis being used, the surgeon's preferences, the patient's existing bony anatomy, and/or other criteria. Additionally, in some embodiments as discussed above, the orthopaedic surgeon may provide additional input to the surgical planning computing device 102 to facilitate or supplement the identification of the one or more anatomical landmarks of the patient's bony anatomy in block 510. To do so, for example, the orthopaedic surgeon may manually annotate the three-dimensional anatomical images to indicate or identify particular anatomical landmarks to be considered by the surgical planning computing device 102. For example, the orthopaedic surgeon may identify or correct a computer-identified location of the dwell point of the patient's tibial medial plateau.

In block 512, the surgical planning computing device 102 determines one or more positioning criteria to be used in the surgical plan. As discussed above, the particular positioning criteria to be used may be determined by the surgical planning computing device 102 based on the orthopaedic prosthesis that is to be used in the orthopaedic surgical procedure, on the particular bone of the patient being operated on, and/or other considerations. The surgical planning computing device 102 subsequently displays the available orthopaedic prosthesis positioning criteria to the orthopaedic surgeon on the display 122 in block 514, who may select one or more positioning criterion. In this way, the orthopaedic surgeon may review the surgical plans (e.g., the updated three-dimensional anatomical images including the three-dimensional model of the orthopaedic prosthesis) resulting from the selection of different positioning criteria and select the most desirable surgical plan for that particular patient.

In block 516, the surgical planning computing device 102 determines whether the orthopaedic surgeon has selected one or more of the positioning criteria. If so, the method 500 advances to block 518 of FIG. 5B. In block 518, the surgical planning computing device 102 generates the surgical plan, or portion thereof. To do so, in block 520, the surgical planning computing device 102 positions a three-dimensional model of the orthopaedic prosthesis (e.g., a three-dimensional model of the tibial insert 200 and the femoral component 300) in the three-dimensional anatomical image of the patient's bony anatomy based on the selected positioning criteria. For example, in block 522, the surgical planning computing device 102 may align one or more features of the three-dimensional model of the orthopaedic prosthesis with respect to a corresponding anatomical landmark identified in block 510 so as to satisfy the positioning criteria.

Figure 7:
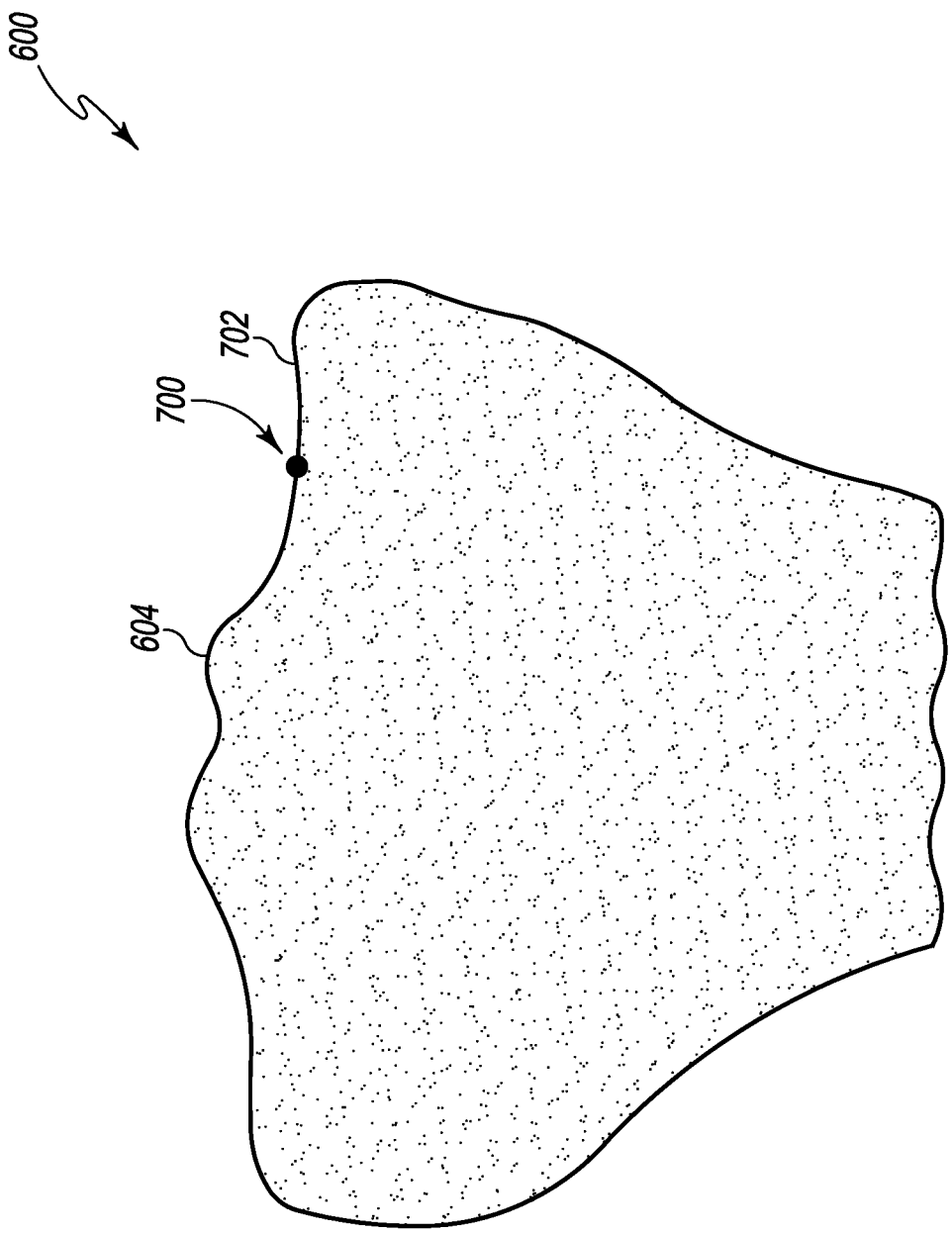
FIG. 7 is a cross-sectional elevation view of a tibia of the patient that may be included in the three-dimensional image of the patient's boney anatomy and including indicia of a dwell point of a tibial plateau of the patient's tibia.
Figure 8:
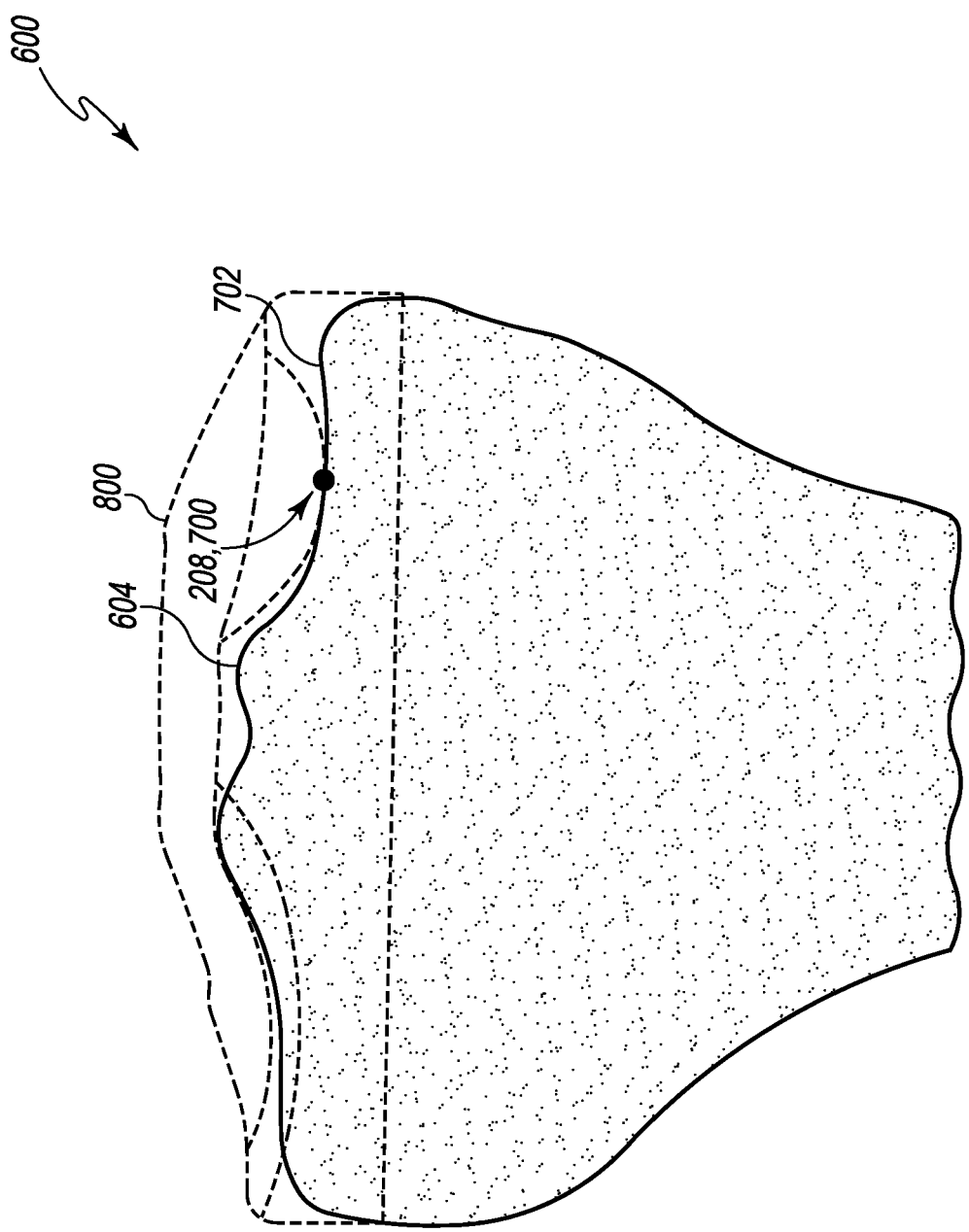
FIG. 8 is a cross-sectional elevation view of the tibia of the patient of FIG. 8 including a three-dimensional model of a tibial component positioned thereon in a dwell point alignment, which may be displayed by the surgical planning computing device of FIG. 1.

As discussed above, the positioning criteria may identify or dictate a particular alignment of an anatomical landmark of the patient's bony anatomy and a corresponding feature of the orthopaedic prosthesis that is to be implanted into the patient. For example, in some embodiments, the position criteria may dictate that the dwell point 208 of the medial articular surface 202 of the tibial insert 200 is aligned with the dwell point of the medial tibial plateau of the patient's tibia. As such, in block 524, the surgical planning computing device 102 may aligns the dwell point 208 of the medial articular surface 202 of the tibial insert 200 with the dwell point of the medial tibial plateau of the patient's tibia. To do so, as shown in FIGS. 7 and 8, the surgical planning computing device 102 is configured to determine the dwell point 700 of the medial tibial plateau 702 of the patient's tibia 604. The dwell point of the patient's tibial plateau generally correlates with the lowest or most-inferior point of the cartilage of the patient's tibial plateau. Of course, it should be appreciated that the dwell "point" may be embodied as a region or collection of points in some embodiments, rather than a single point. Additionally, in some embodiments, the dwell point of the patient's tibia 604 may be dependent upon a particular degree of flexion.

After the surgical planning computing device 102 has determined the dwell point 700, the surgical planning computing device 102 positions a three-dimensional model 800 of the tibial insert 200 in the three-dimensional anatomical image 600 (see FIG. 8) such that dwell point 208 of the medial articular surface 202 of the three-dimensional model 800 of the tibial insert 200 is aligned with (e.g., congruent with) the dwell point 700 of the medial tibial plateau 702 of the tibia 604 of the patient 106. Again, it should be appreciated that the dwell point 208 of the tibial insert 200 may be embodied as a region or collection of points and/or be dependent upon a particular degree of flexion. In such embodiments, the surgical planning computing device 102 may align the three-dimensional model 800 such that the dwell regions are aligned.

Figure 9:
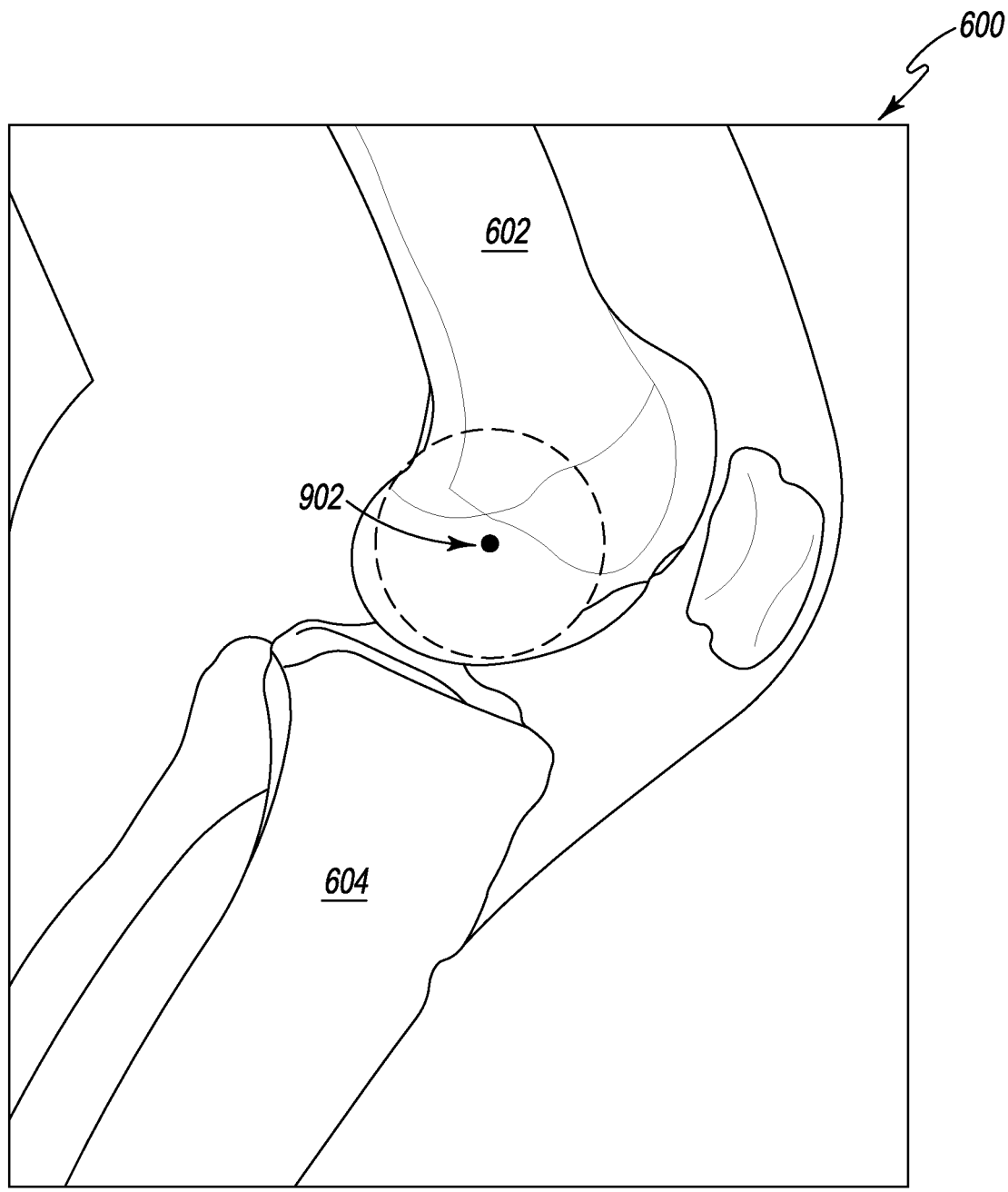
FIG. 9 is an illustration of a three-dimensional image of the patient's boney anatomy of FIG. 6 including indicia of the center of a medial epicondyle of a femur of the patient.
Figure 10:
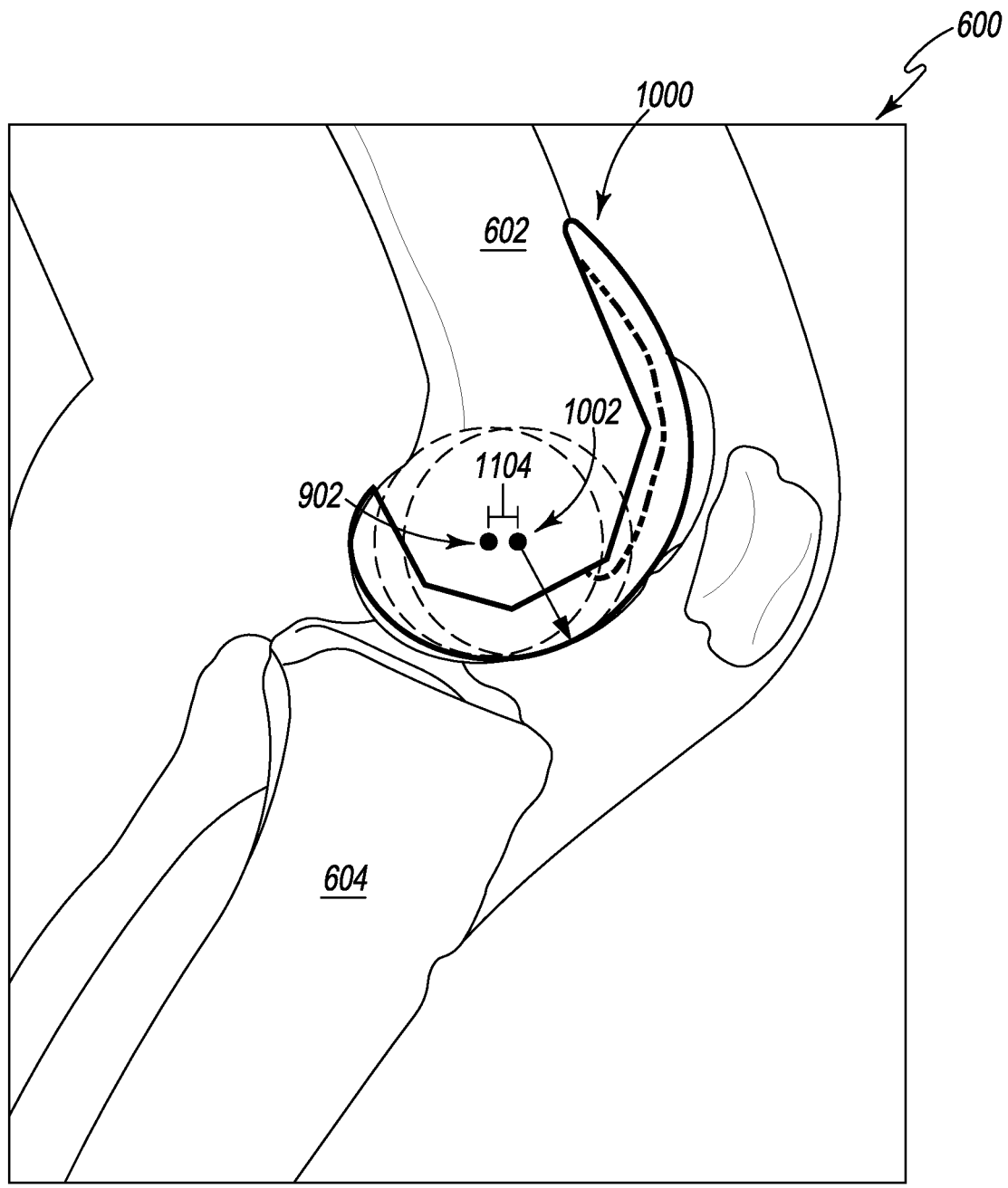
FIG. 10 is an illustration of a three-dimensional image of the patient's boney anatomy of FIG. 9 including a three-dimensional model of a femoral component positioned thereon in an alignment that is based on the center of the medial epicondyle of the femur of the patient.

Referring back to FIG. 5B, the surgical planning computing device 102 also aligns the femoral component 300 to the center of rotation of the patient's medial epicondyle in block 526 (e.g., to the epicondylar axis of the patient's femur). To do so, the surgical planning computing device 102 may utilize one or more position criteria to approximate such positioning. For example, the position criteria may dictate that origin of the constant radius of curvature 310 of the femoral component 300 is offset from the anatomical center of the medial epicondyle of the femur of the patient by a reference amount. As such, in block 528, the surgical planning computing device 102 may align (e.g., offset by a reference amount) the center or origin of the constant radius of curvature 310 of the femoral component 300 with the center of medial epicondyle of the femur of the patient. To do so, as shown in FIG. 9, the surgical planning computing device 102 is configured to determine the anatomical center 902 of the medial epicondyle of the femur 602. Subsequently, as shown in FIG. 10, surgical planning computing device 102 positions the three-dimensional model 100 of the femoral component 300 in the three-dimensional anatomical image 600 such that the origin 1002 of the constant radius of curvature 310 of the three-dimensional model 100 of the femoral component 300 is a reference distance 1104 from the anatomical center 902.

Figure 11:
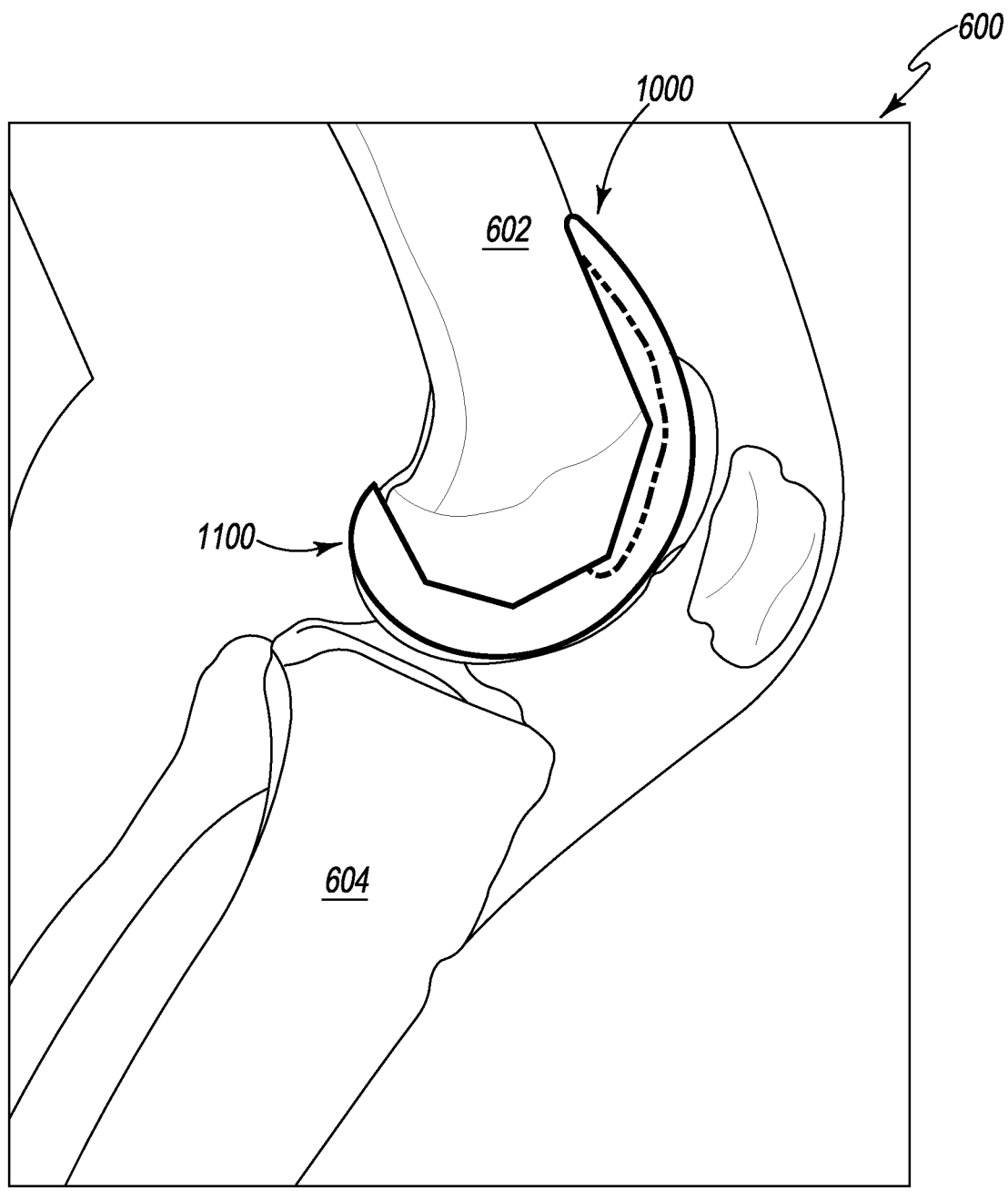
FIG. 11 is an illustration of a three-dimensional image of the patient's boney anatomy of FIG. 6 including a three-dimensional model of a femoral component positioned thereon in a posterior alignment, which may be displayed by the surgical planning computing device of FIG. 1.

Referring back to FIG. 5B, the position criteria may additionally or alternatively dictate that the femoral articular surface of the femoral component 300 defined by the constant radius of curvature 310 is aligned with (e.g., congruent with) the posterior articular surface of a condyle of the patient's femur. As such, in block 530, the surgical planning computing device 102 may align the articular surface of the medial condyle of the femoral component 300 defined by the constant radius of curvature 310 with (e.g., congruent with) the posterior articular surface of the medial condyle of the patient's femur. To do so, as shown in FIG. 11, the surgical planning computing device 102 is configured to position the three-dimensional model 1000 of the femoral component 300 in the three-dimensional anatomical image 600 such that the femoral articular surface of the three-dimensional model 100 of the femoral component 300 defined by the constant radius of curvature 310 is aligned with a posterior articular surface 1100 of a condyle of the femur 602 of the patient 106.

Figure 12:
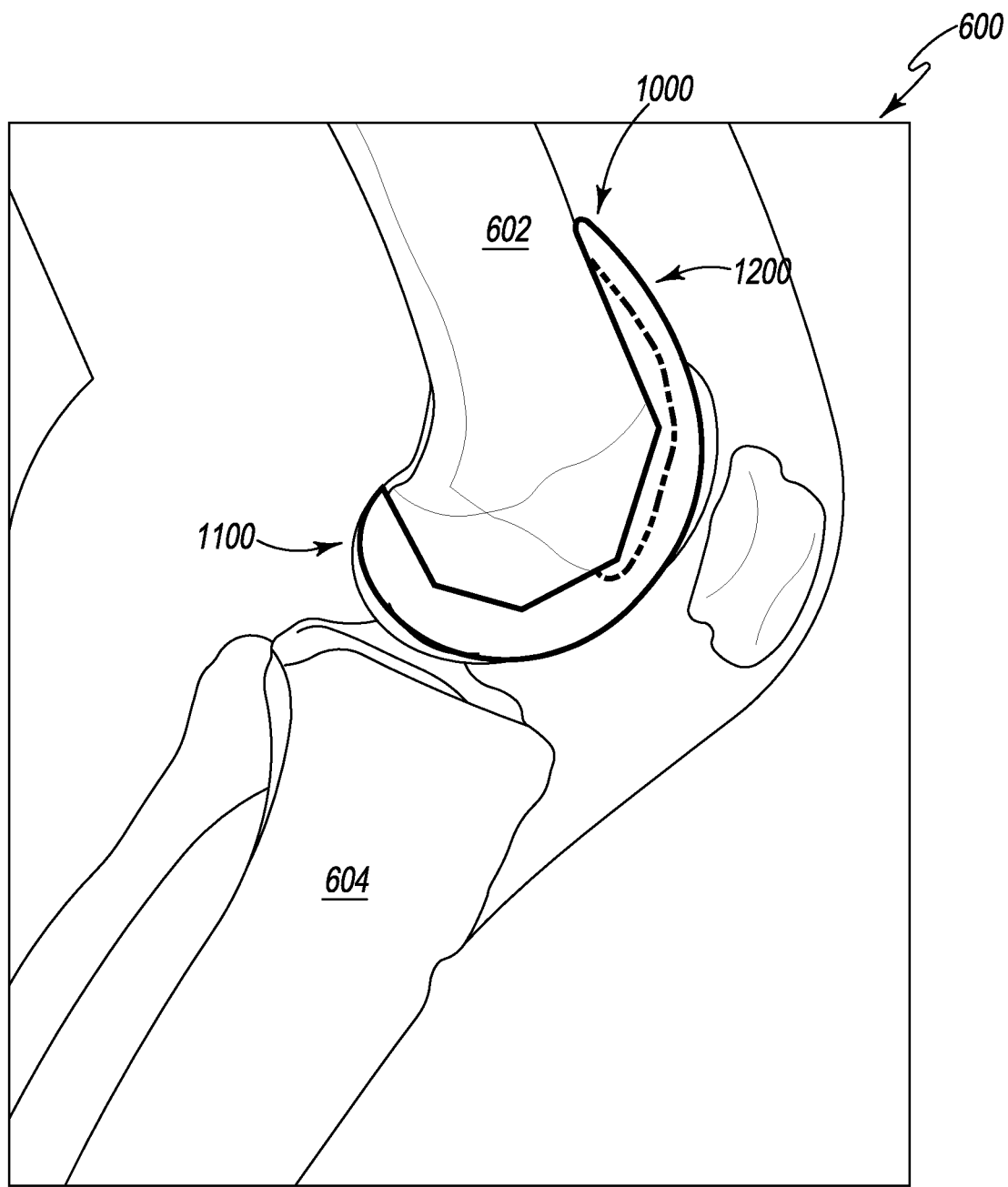
FIG. 12 is an illustration of a three-dimensional image of the patient's boney anatomy of FIG. 6 including a three-dimensional model of a femoral component positioned thereon in an anterior alignment, which may be displayed by the surgical planning computing device of FIG. 1.

Referring back to FIG. 5B, the position criteria may additionally or alternatively dictate that the femoral articular surface of the femoral component 300 defined by the constant radius of curvature 310 is aligned with (e.g., congruent with) the anterior articular surface of a condyle of the patient's femur. As such, in block 532, the surgical planning computing device 102 may align the articular surface of the medial condyle of the femoral component 300 defined by the constant radius of curvature 310 with (e.g., congruent with) the anterior articular surface of the medial condyle of the patient's femur. To do so, as shown in FIG. 12, the surgical planning computing device 102 is configured to position the three-dimensional model 100 of the femoral component 300 in the three-dimensional anatomical image 600 such that the femoral articular surface of the three-dimensional model 100 of the femoral component 300 defined by the constant radius of curvature 310 is aligned with an anterior articular surface 1200 of a condyle of the femur 602 of the patient 106.

Figure 13:
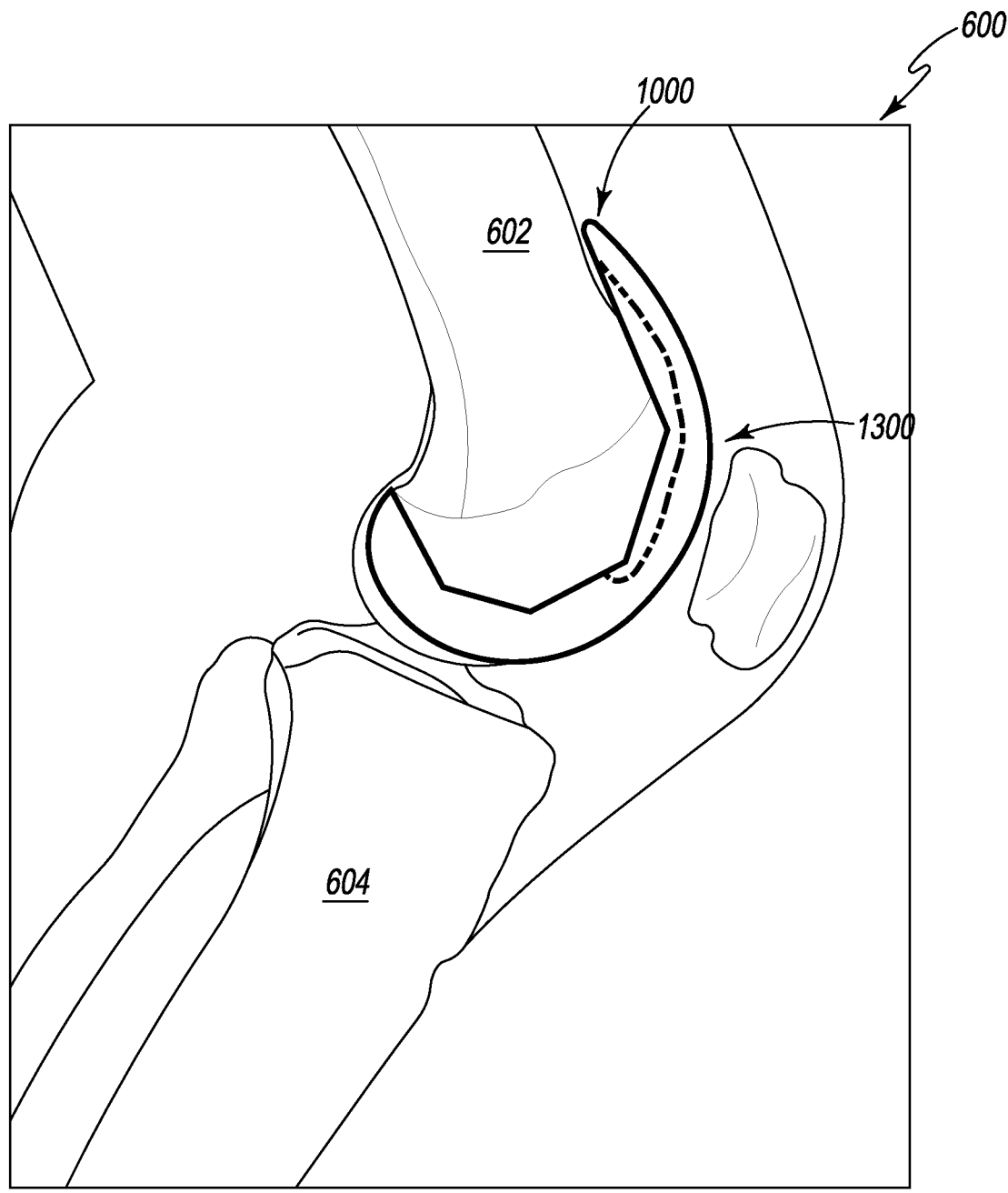
FIG. 13 is an illustration of a three-dimensional image of the patient's boney anatomy of FIG. 6 including a three-dimensional model of a femoral component positioned thereon in a patellofemoral alignment, which may be displayed by the surgical planning computing device of FIG. 1.

Referring back to FIG. 5B, the position criteria may additionally or alternatively dictate that that articular surface of the patellofemoral surface of the femoral component 300 is aligned (e.g., congruent with) the patellofemoral surface of the patient's femur. As such, in block 534, the surgical planning computing device 102 may align the articular surface of the patellofemoral surface of the femoral component 300 defined by the constant radius of curvature 310 with (e.g., congruent with) the patellofemoral surface of the patient's femur. To do so, as shown in FIG. 13, the surgical planning computing device 102 is configured to position the three-dimensional model 1000 of the femoral component 300 in the three-dimensional anatomical image 600 such that the patellofemoral surface of the three-dimensional model 100 of the femoral component 300 is aligned with the patellofemoral surface of the femur 602 of the patient 106.

Figure 14:
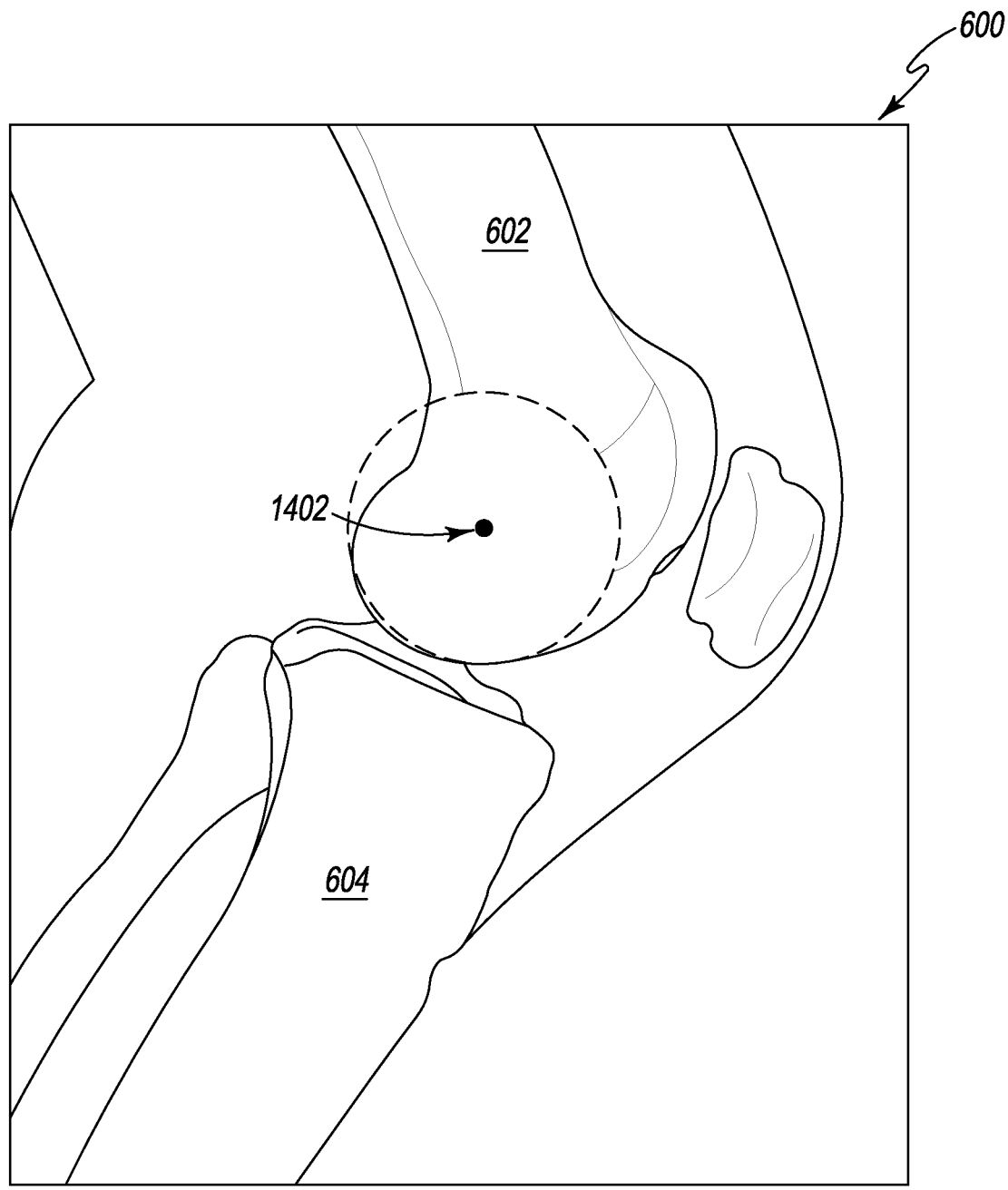
FIG. 14 is an illustration of a three-dimensional image of the patient's boney anatomy of FIG. 6 including indicia of the center of a lateral epicondyle of a femur of the patient.
Figure 15:
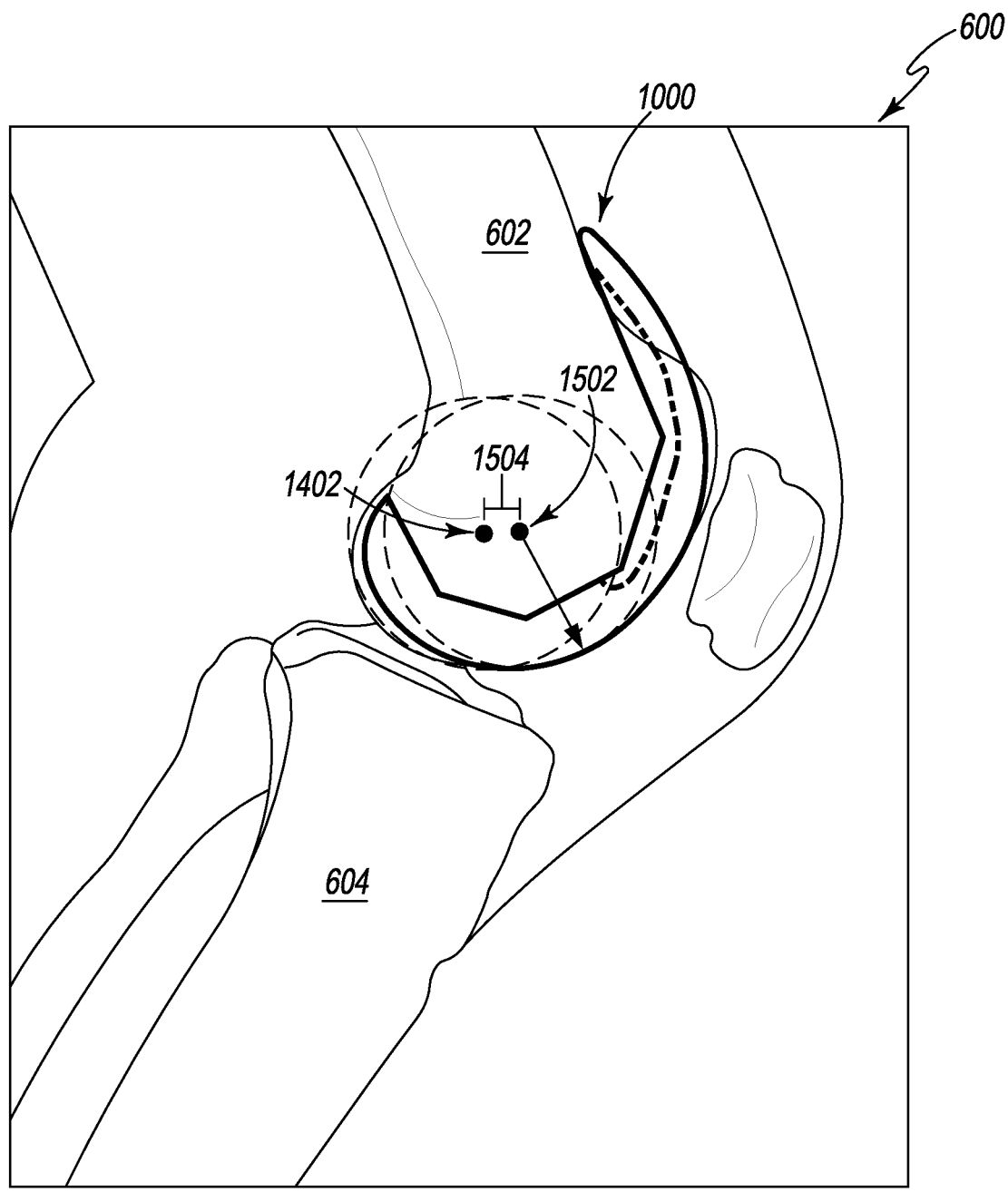
FIG. 15 is an illustration of a three-dimensional image of the patient's boney anatomy of FIG. 14 including a three-dimensional model of a femoral component positioned thereon in an alignment that is based on the center of the lateral epicondyle of the femur of the patient.

In some embodiments, as discussed above, the lateral condyle of the femoral component 300 may be allowed to float and subsequently positioned during the orthopaedic surgery using a "lateral float" procedure. That is, the final positioning of the lateral condyle of the femoral component 300 may be determined intra-operatively based on the flexion and extension movement of the artificial joint. However, in other embodiments, the position criteria may additionally dictate that origin of the constant radius of curvature 310 of the lateral condyle of the femoral component 300 is offset from the anatomical center of the lateral epicondyle of the femur of the patient by a reference amount. As such, in block 536, the surgical planning computing device 102 may align (e.g., offset by a reference amount) the center or origin of the constant radius of curvature 310 of the lateral condyle of the femoral component 300 with the center of lateral epicondyle of the femur of the patient. To do so, as shown in FIG. 14, the surgical planning computing device 102 is configured to determine the anatomical center 1402 of the lateral epicondyle of the femur 602. Subsequently, as shown in FIG. 15, surgical planning computing device 102 positions the three-dimensional model 100 of the femoral component 300 in the three-dimensional anatomical image 600 such that the origin 1502 of the constant radius of curvature 310 of the lateral condyle of the three-dimensional model 100 of the femoral component 300 is a reference distance 1504 from the anatomical center 1402 of the lateral condyle.

Referring now back to FIG. 5B, after the surgical planning computing device 102 has positioned the three-dimensional model of the orthopaedic prosthesis in the three-dimensional anatomical image based on the selected positioning criteria, the method 500 advances to block 538 of FIG. 5C, in some embodiments. In block 538, the surgical planning computing device 102 generates positioning data that defines orthopaedic coordinates (e.g., anterior-posterior and medial-lateral coordinates) at which a feature of the orthopaedic prosthesis should be located to match the location of the three-dimensional model of the orthopaedic prosthesis determined in block 520. The particular feature of the orthopaedic prosthesis may or may not be the same feature identified in the positioning criteria used to position the three-dimensional model in the three-dimensional anatomical image.

Additionally, in some embodiments, the surgical planning computing device 102 may generate instructions for automated surgical instruments in block 540. The instructions are useable by the automated surgical instruments to perform an orthopaedic surgical procedure to implant the orthopaedic prosthesis (e.g., the tibial insert 200 and/or femoral component 300) in the patient's anatomy consistent with the generated surgical plan. For example, the instructions may be embodied as instructions for an orthopaedic surgical saw to perform bone cuts required for the implantation of the tibial insert 200 and/or femoral component 300 consistent with the generated surgical plan.

In block 542, the surgical planning computing device 102 presents the surgical plan, or portion thereof, to the orthopaedic surgeon. For example, in block 544, the surgical planning computing device 102 may display an updated three-dimensional anatomical image of the patient's bony anatomy that includes the three-dimensional model of the orthopaedic prosthesis located in the position determined in block 518. Additionally, in some embodiments, the surgical planning computing device 102 may display the positioning data determined in block 538.

Figure 5D:
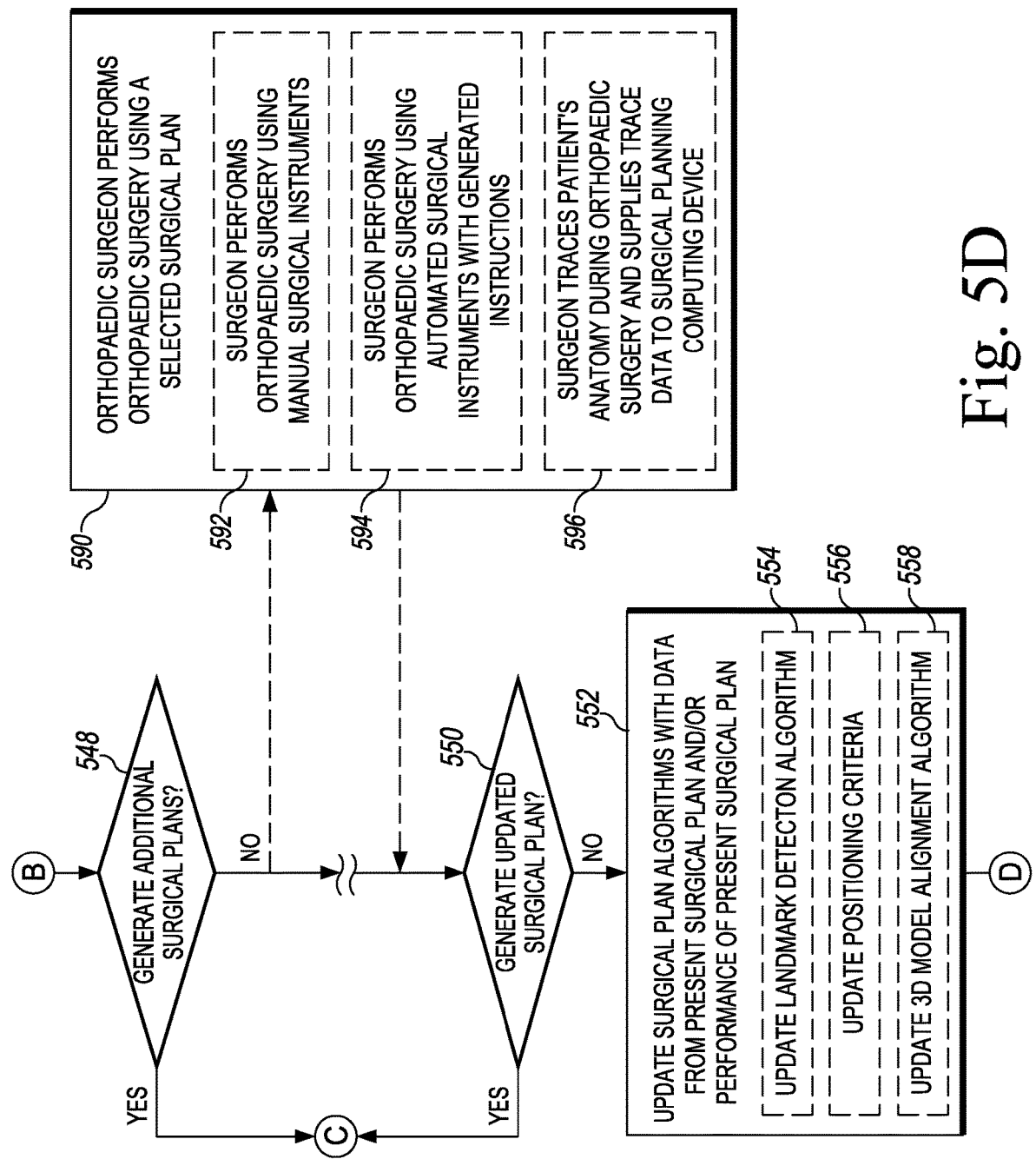

In block 548 of FIG. 5D, the orthopaedic surgeon may review the updated three-dimensional anatomical image to determine whether such positioning is acceptable and/or whether additional surgical plans (e.g., with alternative positioning) are desirable. If additional surgical plans are desired, the method 500 loops back to block 510 of FIG. 5A in which the surgical planning computing device 102 again identifies anatomical landmarks of the patient's bony anatomy in the three-dimensional anatomical image. In subsequent iterations of the method 500, the surgical planning computing device 102 may utilize additional information provided by the orthopaedic surgeon as discussed below and/or alternative positioning criteria to generate alternative surgical plans, which may include alternative positioning of the orthopaedic prosthesis.

If, however, no additional surgical plans are desired, the method 500 advances to block 590 in which the orthopaedic surgeon performs the orthopaedic surgery using the selected surgical plan. To do so, the orthopaedic surgeon may perform the orthopaedic surgery using manual surgical instruments and the generated surgical plan in block 592. For example, the orthopaedic surgeon may perform the orthopaedic surgery using the updated three-dimensional image including the three-dimensional model of the orthopaedic prosthesis as a guide to positioning the actual orthopaedic prosthesis. Additionally or alternatively, the orthopaedic surgeon may utilize the positioning date generated in block 538 as measurements for aligning the actual orthopaedic prosthesis.

Alternatively, block 594, the orthopaedic surgeon may perform the orthopaedic surgery using automated surgical instruments and the generated surgical plan in block 594. In such embodiments, as discussed above, the surgical planning computing device 102 may generate instructions for automated surgical instruments in block 540, and the orthopaedic surgeon may use the automated tools equipped with the instructions to perform the orthopaedic surgical procedure. For example; the orthopaedic surgeon may utilize an automated surgical saw having instructions that define particular bone cuts to be performed. Of course, it should be appreciated that the orthopaedic surgeon may use a combination of manual and automated surgical tools in some embodiments.

In some embodiments, in block 596, the orthopaedic surgeon may trace and/or annotate the patient's bony anatomy during performance of the orthopaedic surgical procedure and supply such trace data to the surgical planning computing device 102. In such embodiments, the surgical planning computing device 102 may utilize the trace data to improve the accuracy of the anatomical landmark identification of block 510, the determination of the orthopaedic prosthesis positioning criteria of block 512, and/or the positioning of the three-dimensional model of the orthopaedic prosthesis of block 520.

It should be appreciated that although the functions of blocks 590-596 are performed by the orthopaedic surgeon and not by the surgical planning computing device 102, they have been included in the method 500 for clarity of description. However, after the orthopaedic surgeon has completed the orthopaedic surgery or anytime during the performance of block 590, the surgical planning computing device 102 may determine whether to update the surgical plan in block 550. For example, the surgical planning computing device 102 may determine to update the surgical plan based on information (e.g., trace data) received from the orthopaedic surgeon during performance of the orthopaedic surgery in block 590 and/or in response to a selection by the orthopaedic surgeon. If so, the method 500 loops back to block 510 of FIG. 5A in which the surgical planning computing device 102 again identifies anatomical landmarks of the patient's bony anatomy in the three-dimensional anatomical image. In subsequent iterations of the method 500, the surgical planning computing device 102 may utilize the additional information provided by the orthopaedic surgeon to generate an updated surgical plan. In this way, the orthopaedic surgeon may improve the generated surgical plan intra-operatively with newly obtained information.

If, however, and updated surgical plan is not desired, the method 500 advances to block 552 in some embodiments. In block 552, the surgical planning computing device 102 updates one or more surgical plan algorithms with data or information obtained from the present surgical plan and/or performance of the present surgical plan. For example, in some embodiments in block 554, the surgical planning computing device 102 may update the algorithm(s) used to detect or identify the anatomical landmarks of the patient's bony anatomy in block 510. To do so, the surgical planning computing device 102 may use the tracing data received from the orthopaedic surgeon in block 596 and/or other data received from the orthopaedic surgeon (e.g., a grading of the present identification).

Additionally, in some embodiments in block 556, the surgical planning computing device 102 may update the positioning criteria that identifies the particular alignment of an anatomical landmark of the patient's bony anatomy and a corresponding feature of the orthopaedic prosthesis. To do so, the surgical planning computing device 102 may update the positioning criteria with any information received from the orthopaedic surgeon, such as adjustments to the positioning of the orthopaedic prosthesis performed intra-operatively by the orthopaedic surgeon.

Additionally, in some embodiments in block 558, the surgical planning computing device 102 may update the alignment algorithm used to align the three-dimensional model of the orthopaedic prosthesis with the corresponding anatomical landmark of the patient's bony anatomy. To do so, the surgical planning computing device 102 may update the alignment algorithm with any information received from the orthopaedic surgeon, such as adjustments to the positioning of the orthopaedic prosthesis performed intra-operatively by the orthopaedic surgeon as discussed above.

In this way, accuracy of surgical plans generated by the surgical planning computing device 102 may be improved overtime based on feedback from the orthopaedic surgeon and/or data gathered during performance of the orthopaedic surgery. The surgical planning computing device 102 may utilize any suitable artificial intelligence or machine learning algorithm to update and improve the generation of the surgical plan based on such feedback and additional data.

It should be further appreciated that the generation of the surgical plan by the surgical planning computing device 102 may be performed prior to surgery and outside of the operating room and/or during the performance of the orthopaedic surgery and/or within the operating room. For example, as discussed above, the surgical planning computing device 102 may update the surgical plan intraoperatively based on feedback from the orthopaedic surgeon and/or additional information obtained during the performance of the orthopaedic surgery.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A surgical planning computing system for generating a surgical plan for an orthopaedic surgical procedure, the surgical planning computing system comprising:
   one or more processors; and
   memory having stored therein a plurality of instructions that, in response to execution by the one or more processors, cause the surgical planning computing system to:
      identify a dwell point of a medial tibial plateau of a patient's tibia captured in a three-dimensional anatomical image of the patient's bony anatomy;
      identify a center of rotation of a medial condyle of a patient's femur a captured in the three-dimensional anatomical image,
      determine positioning criteria for a medial pivoting orthopaedic prosthesis that is to be used in the orthopaedic surgical procedure, wherein the medial pivoting orthopaedic prosthesis includes a tibial insert and a femoral component and wherein the positioning criteria identifies (i) an alignment between the dwell point of the medial articular surface of the tibial insert and the dwell point of the medial tibial plateau of the patient's tibia and (ii) an alignment of a feature of a medial condyle of the femoral component based on the center of rotation of the medial condyle of the patient's femur,
      position a three-dimensional model of the tibial insert and of the femoral component in the three-dimensional anatomical image based on the positioning criteria to generate an updated three-dimensional anatomical image that includes the three-dimensional model of the orthopaedic prosthesis; and
      display the updated three-dimensional anatomical image.

2. The surgical planning computing system of claim 1, wherein to position the three-dimensional model of the tibial insert in the three-dimensional anatomical image based on the positioning criteria comprises to position the three-dimensional model of the tibial insert in the three-dimensional anatomical image such that the dwell point of the medial articular surface of the tibial insert is aligned with the dwell point of the medial tibial plateau of the patient's tibia included in the three-dimensional anatomical image.

3. The surgical planning computing system of claim 2, wherein to position the three-dimensional model of the femoral component in the three-dimensional anatomical image based on the positioning criteria comprises to position the three-dimensional model of the femoral component in the three-dimensional anatomical image such that a center of a constant radius of curvature that defines an articular surface of the medial condyle of the femoral component is offset from an anatomical center of the medial epicondyle of the patient's femur included in the three-dimensional anatomical image by a reference amount.

4. The surgical planning computing system of claim 2, wherein to position the three-dimensional model of the femoral component in the three-dimensional anatomical image based on the positioning criteria comprises to position the three-dimensional model of the femoral component in the three-dimensional anatomical image such that an articular surface of the medial condyle of the femoral component that is defined by a constant radius of curvature is aligned with a posterior articular surface of the medial condyle of the patient's femur included in the three-dimensional anatomical image.

5. The surgical planning computing system of claim 2, wherein to position the three-dimensional model of the femoral component in the three-dimensional anatomical image based on the positioning criteria comprises to position the three-dimensional model of the femoral component in the three-dimensional anatomical image such that an articular surface of the medial condyle of the femoral component that is defined by a constant radius of curvature is aligned with an anterior articular surface of the medial condyle of the patient's femur included in the three-dimensional anatomical image.

6. The surgical planning computing system of claim 2, wherein to position the three-dimensional model of the femoral component in the three-dimensional anatomical image based on the positioning criteria comprises to position the three-dimensional model of the femoral component in the three-dimensional anatomical image such that an articular surface of a patellofemoral surface of the femoral component is aligned with a patellofemoral surface of the patient's femur included in the three-dimensional anatomical image.

7. The surgical planning computing system of claim 2, wherein to position the three-dimensional model of the femoral component in the three-dimensional anatomical image based on the positioning criteria comprises to position the three-dimensional model of the femoral component in the three-dimensional anatomical image such that a center of a constant radius of curvature that defines an articular surface of a lateral condyle of the femoral component is offset from an anatomical center of the lateral epicondyle of the patient's femur included in the three-dimensional anatomical image by a reference amount.

8. The surgical planning computing system of claim 1, wherein the plurality of instructions, in response to execution, further cause the computing system to generate positioning data that defines orthopaedic coordinates at which the feature of the orthopaedic prosthesis should be located on a bone of the patient's anatomy.

9. A method for performing an orthopaedic surgery on a patient, the method comprising:
obtaining a three-dimensional anatomical image of a patient's bony anatomy in which medial pivoting orthopaedic prosthesis is to be implanted during the orthopaedic surgery, wherein the three-dimensional anatomical image includes a three-dimensional image of a tibia and corresponding femur of the patient;
operating a surgical planning computing system to (i) identify a dwell point of a medial tibial plateau of the patient's tibia in the three-dimensional anatomical image, (ii) identify a center of rotation of a medial condyle of the patient's femur in the three-dimensional anatomical image, (iii) determine positioning criteria for the medial pivoting orthopaedic prosthesis, wherein the medial pivoting orthopaedic prosthesis includes a tibial insert and a femoral component and wherein the positioning criteria identifies (a) an alignment between the dwell point of the medial articular surface of the tibial insert and the dwell point of the medial tibial plateau of the patient's tibia and (b) an alignment of a feature of a medial condyle of the femoral component based on the center of rotation of the medial condyle of the patient's femur, and (iv) position a three-dimensional model of the tibial insert and of the femoral component in the three-dimensional anatomical image based on the positioning criteria to generate an updated three-dimensional anatomical image that includes the three-dimensional model of the orthopaedic prosthesis; and
performing the orthopaedic surgery to implant the orthopaedic prosthesis into the patient's bone using the updated three-dimensional anatomical image as a surgical plan for the orthopaedic surgery.

10. The method of claim 9, wherein to position the three-dimensional model of the tibial insert in the three-dimensional anatomical image based on the positioning criteria comprises to position the three-dimensional model of the tibial insert in the three-dimensional anatomical image such that the dwell point of the medial articular surface of the tibial insert is aligned with the dwell point of the medial tibial plateau of the patient's tibia included in the three-dimensional anatomical image.

11. The method of claim 10, wherein to position the three-dimensional model of the femoral component in the three-dimensional anatomical image based on the positioning criteria comprises to position the three-dimensional model of the femoral component in the three-dimensional anatomical image such that a center of a constant radius of curvature that defines an articular surface of the medial condyle of the femoral component is offset from an anatomical center of the medial epicondyle of the patient's femur included in the three-dimensional anatomical image by a reference amount.

12. The method of claim 10, wherein to position the three-dimensional model of the femoral component in the three-dimensional anatomical image based on the positioning criteria comprises to position the three-dimensional model of the femoral component in the three-dimensional anatomical image such that an articular surface of the medial condyle of the femoral component that is defined by a constant radius of curvature is aligned with a posterior articular surface of the medial condyle of the patient's femur included in the three-dimensional anatomical image.

13. The method of claim 10, wherein to position the three-dimensional model of the femoral component in the three-dimensional anatomical image based on the positioning criteria comprises to position the three-dimensional model of the femoral component in the three-dimensional anatomical image such that an articular surface of the medial condyle of the femoral component that is defined by a constant radius of curvature is aligned with an anterior articular surface of the medial condyle of the patient's femur included in the three-dimensional anatomical image.

14. The method of claim 10, wherein to position the three-dimensional model of the femoral component in the three-dimensional anatomical image based on the positioning criteria comprises to position the three-dimensional model of the femoral component in the three-dimensional anatomical image such that an articular surface of a patellofemoral surface of the femoral component is aligned with a patellofemoral surface of the patient's femur included in the three-dimensional anatomical image.

15. The method of claim 10, wherein to position a three-dimensional model of the femoral component in the three-dimensional anatomical image based on the positioning criteria comprises to position the three-dimensional model of the femoral component in the three-dimensional anatomical image such that a center of a constant radius of curvature that defines an articular surface of a lateral condyle of the femoral component is offset from an anatomical center of the lateral epicondyle of the patient's femur included in the three-dimensional anatomical image by a reference amount.

16. One or more non-transitory, machine-readable storage media comprising a plurality of instructions stored thereon that, in response to execution by a computing system, cause the computing system to:
identify a dwell point of a medial tibial plateau of a patient's tibia captured in a three-dimensional anatomical image of the patient's bony anatomy;
identify a center of rotation of a medial condyle of a patient's femur a captured in the three-dimensional anatomical image,
determine positioning criteria for a medial pivoting orthopaedic prosthesis that is to be used in the orthopaedic surgical procedure, wherein the medial pivoting orthopaedic prosthesis includes a tibial insert and a femoral component and wherein the positioning criteria identifies (i) an alignment between the dwell point of the medial articular surface of the tibial insert and the dwell point of the medial tibial plateau of the patient's tibia and (ii) an alignment of a feature of a medial condyle of the femoral component based on the center of rotation of the medial condyle of the patient's femur,
position a three-dimensional model of the tibial insert and of the femoral component in the three-dimensional anatomical image based on the positioning criteria to generate an updated three-dimensional anatomical image that includes the three-dimensional model of the orthopaedic prosthesis; and
display the updated three-dimensional anatomical image.

17. The one or more non-transitory, machine-readable storage media of claim 16, wherein to position the three-dimensional model of the tibial insert in the three-dimensional anatomical image based on the positioning criteria comprises to position the three-dimensional model of the tibial insert in the three-dimensional anatomical image such that the dwell point of the medial articular surface of the tibial insert is aligned with the dwell point of the medial tibial plateau of the patient's tibia included in the three-dimensional anatomical image.

18. The one or more non-transitory, machine-readable storage media of claim 17, wherein to position the three-dimensional model of the femoral component in the three-dimensional anatomical image based on the positioning criteria comprises to position the three-dimensional model of the femoral component in the three-dimensional anatomical image such that a center of a constant radius of curvature that defines an articular surface of the medial condyle of the femoral component is offset from an anatomical center of the medial epicondyle of the patient's femur included in the three-dimensional anatomical image by a reference amount.

19. The one or more non-transitory, machine-readable storage media of claim 17, wherein to position the three-dimensional model of the femoral component in the three-dimensional anatomical image based on the positioning criteria comprises to position the three-dimensional model of the femoral component in the three-dimensional anatomical image such that an articular surface of the medial condyle of the femoral component that is defined by a constant radius of curvature is aligned with a posterior articular surface of the medial condyle of the patient's femur included in the three-dimensional anatomical image.

20. The one or more non-transitory, machine-readable storage media of claim 17, wherein to position the three-dimensional model of the femoral component in the three-dimensional anatomical image based on the positioning criteria comprises to position the three-dimensional model of the femoral component in the three-dimensional anatomical image such that an articular surface of the medial condyle of the femoral component that is defined by a constant radius of curvature is aligned with an anterior articular surface of the medial condyle of the patient's femur included in the three-dimensional anatomical image.

* * * * *